United States Patent [19]

Kuhla et al.

[11] Patent Number: 4,529,723

[45] Date of Patent: Jul. 16, 1985

[54] BICYCLIC BENZENOID AMINOALKYLENE ETHERS AND THIOETHERS, PHARMACEUTICAL COMPOSITIONS AND USE

[75] Inventors: Donald E. Kuhla, Doylestown; Henry F. Campbell, Lansdale; William L. Studt, Harleysville, all of Pa.

[73] Assignee: William H. Rorer, Inc., Fort Washington, Pa.

[21] Appl. No.: 489,702

[22] Filed: Apr. 29, 1983

[51] Int. Cl.$^3$ .................. A61K 31/41; A61K 31/535; C07D 249/12; C07D 413/12
[52] U.S. Cl. .................. 514/212; 514/222; 514/232; 514/237; 514/255; 514/319; 514/383; 514/228; 544/58.5; 544/60; 544/132; 544/366; 546/205; 546/206; 548/267; 260/245.5
[58] Field of Search .............. 544/60, 58.5, 132, 366; 546/205, 206; 548/267; 260/245.5; 424/248.5, 248.52, 248.56, 267, 269, 273 R, 273 P

[56] References Cited

U.S. PATENT DOCUMENTS 4,318,913  3/1982  Clitherow et al. .................. 548/267

*Primary Examiner*—Robert W. Ramsuer
*Attorney, Agent, or Firm*—James A. Nicholson; Alexis Barron; Martin F. Savitzky

[57] ABSTRACT

A class of bicyclic benzenoid aminoalkylene ether and thioether compounds exhibiting pharmacological activity including anti-secretory and anti-ulcerogenic activity, pharmaceutical compositions comprising these compounds, and methods for the treatment of gastrointestinal hyperacidity and ulcerogenic disorders in mammals using said compositions are disclosed.

21 Claims, No Drawings

BICYCLIC BENZENOID AMINOALKYLENE ETHERS AND THIOETHERS, PHARMACEUTICAL COMPOSITIONS AND USE

FIELD OF THE INVENTION

This invention relates to a class of bicyclic benzenoid compounds characterized by an ether or thioether substituent on the phenyl ring and an exocyclic nitrogen substituent on the other ring of the bicyclic ring system and methods for the treatment of physiological disorders, including gastrointestinal disorders in humans and other mammals.

REPORTED DEVELOPMENTS

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid are implicated as causes of these disorders. Traditional treatment of these disorders has involved the administration of antacids to neutralize the excess gastric acid and the administration of antisecretory drugs which generally reduce the production of all gastric secretions.

In the last few years, the treatment of gastrointestinal disorders such as peptic ulcer has changed to include the use of anti-secretory drugs which selectively block the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al. (Nature 1972, 236, 385). The $H_1$-receptor is involved in the bronchial and gastrointestinal smooth muscle stimulative action of histamine. Drugs which block this action are labelled "antihistamines" (e.g. mepyramine).

Black et al., cited above, described the group of substances which act at histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, and British published patent application GB No. 2067987A, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the action of strong gastric acid. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research*, Vol. 8 (Raven Press, N.Y. 1980), and Robert et al., "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl-carbamoylcarboxylic acids, esters and imides described in U.S. Pat. No. 4,321,372.

Compounds of the present invention comprise bicyclic benzenoids which exhibit anti-secretory activity, $H_2$-receptor antagonist activity, anti-ulcer activity and cytoprotective activity.

SUMMARY OF THE INVENTION

This invention comprises a class of compounds according to Formula I

Formula I

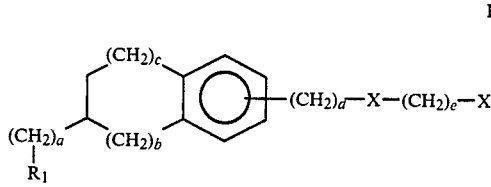

wherein:

a is 0, 1 or 2;
b is 0 or 1;
c is 1-b, 2-b or 3-b;
d is 0 or 1;
e is 2, 3 or 4;
X is oxygen, sulfur,

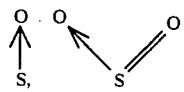

or $CH_2$;
Z is $-NHR_4$,

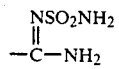

or $-CN$;
$R_1$ is $-NR_2R_3$,

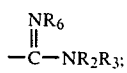

$R_2$ and $R_3$ are each independently H or alkyl, or both together with the nitrogen to which they are attached form a 5, 6 or 7-membered ring which may include one to three additional hetero atoms of N, O or S;

R$_4$ is selected from the group consisting of H,

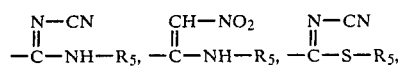

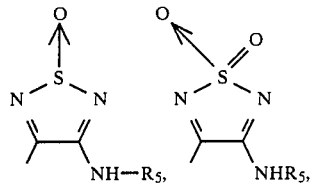

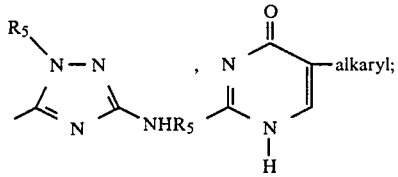

R$_5$ is H or lower alkyl;

R$_6$ is H or lower alkyl or R$_6$ together with R$_2$ are ethylene or propylene and form a 5 or 6 membered ring with the nitrogen atoms to which they are attached; or a pharmaceutically acceptable salt thereof.

Compounds within the scope of Formula I exhibit physiological activity in mammals including anti-secretory activity, histamine H$_2$-receptor antagonist activity, anti-ulcer activity and cytoprotective activity.

This invention also relates to methods for the treatment and prevention of gastrointestinal hyperacidity and ulcerogenic disorders in humans and other mammals comprising administering to a patient an effective amount of a compound within the description of Formula I.

DETAILED DESCRIPTION OF THE INVENTION

Preferred classes of compounds according to this invention are described by Formulae II, III, IV and V:

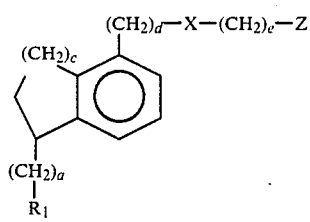
Formula II or;

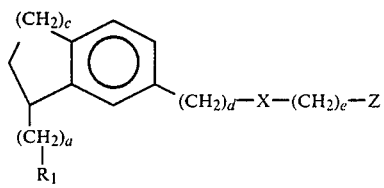
Formula III wherein:
a is 0, 1 or 2;
c is 1, 2 or 3;
d is 0 or 1;
e is 2, 3 or 4;
x is oxygen or sulfur;
Z is NHR$_4$ or

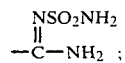

R$_1$ is —NR$_2$R$_3$;
R$_2$, R$_3$, R$_4$ and R$_5$ are as described above.

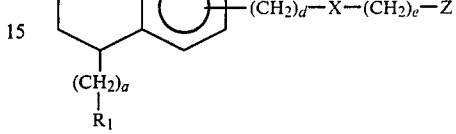
Formula IV

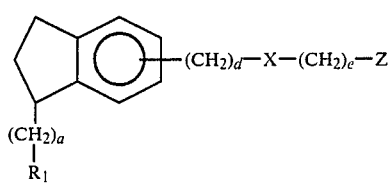
Formula V wherein:
a is 0, 1 or 2;
d is 0 or 1;
e is 2, 3 or 4;
X is oxygen or sulfur;
Z is NHR$_4$ or

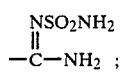

R$_1$ is —NR$_2$R$_3$;
R$_2$, R$_3$, R$_4$ and R$_5$ are as described above.

A most preferred class of compounds within the scope of Formula I comprises the compounds of Formula I wherein:
a is 0;
b is 0;
d is 0;
e is 3;
X is oxygen; and
Z is —NHR$_4$ or

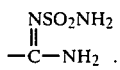

A preferred subclass of compounds is described by Formula IV or V, wherein:
a and d are 0;
e is 3; and
X is oxygen.

Another preferred subclass of compounds is described by Formula IV or V, wherein:
a is 0;
d is 1;
e is 2; and
X is sulfur.

A most preferred class of compounds is described by Formula VI.

Formula VI

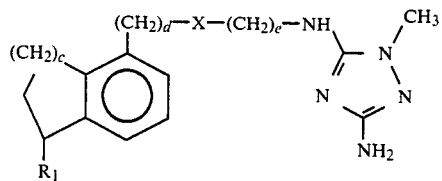

wherein:
c is 1 or 2;
d is 0 or 1;
e is 2, 3 or 4;
X is oxygen or sulfur;
$R_1$ is $-NR_2R_3$;
$R_2$ and $R_3$ together with the nitrogen to which they are attached form a 5, 6 or 7 membered heterocyclic ring which may include one to three additional hetero atoms of N, O or S; or a pharmaceutically acceptable salt thereof.

A particularly interesting class of compounds according to Formula VI comprises those compounds wherein $R_1$ is N-piperidyl, N-pyrrolidinyl, N-morpholinyl or N-azepinyl.

The compounds of Formulae I to VI may also form hydrates and exhibit tautomerism. Formulae I to VI are intended to encompass all hydrates and tautomers, as well as any diastereomers and optical enantiomers.

As employed above and throughout the disclosure, the following terms, unless otherwise indicated, shall be understood to have the following meanings:

"Lower alkyl" means an alkyl group as above, having 1 to about 4 carbon atoms. Examples of lower alkyl groups are methyl, ethyl, n-propyl, isopropyl, butyl, sec-butyl, and tert-butyl.

"5, 6 or 7 membered heterocyclic ring" means a nitrogen-containing ring of the formula

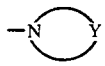

where Y is alkylene or alkylidinyl having from one to six carbon atoms, and may include one to three atoms of N, O or S. Exemplary heterocyclic groups include piperidyl, pyrrolidinyl, morpholinyl, azepinyl, pyrrolyl, imidazolyl, pyrazolyl, and thiamorpholinyl.

Representative examples of compounds of this invention are listed below in Tables A, B, C, D, E and F.

TABLE A wherein substitution may be at the 5, 6, 7 or 8 position

| $R_1$ | Z |
|---|---|
| $-N(CH_3)_2$ | $-NH-\overset{NCN}{\underset{\|}{C}}-NHCH_3$ |
| -N⟨piperidyl⟩ | $-NH-\overset{NCN}{\underset{\|}{C}}-NH_2$ |
| -N⟨pyrrolidinyl⟩ | $-NH-\overset{CHNO_2}{\underset{\|}{C}}-NHCH_3$ |
| $-NH_2$ | $-NH-\overset{CHNO_2}{\underset{\|}{C}}-NH_2$ |
| -N⟨pyrrolidinyl⟩ | $-NH-\overset{N-CN}{\underset{\|}{C}}-S-CH_3$ |
| -N⟨piperidyl⟩ | $-NH-\overset{N-CN}{\underset{\|}{C}}-S-CH_3$ |

TABLE A-continued

| $R_1$ | Z |
|---|---|
| -N⟨morpholinyl⟩ | $-NH\overset{N-CN}{\underset{\|}{C}}-S-CH_3$ |
| $-N(CH_3)_2$ | $-NH\overset{N-CN}{\underset{\|}{C}}-S-CH_3$ |
| $-NHCH_3$ | (pyrimidinone with methylenedioxyphenyl) |
| -N⟨piperidyl⟩ | (pyrimidinone with methylpyridyl) |
| -N⟨pyrrolidinyl⟩ | (thiadiazole S-oxide with NH, NH₂) |

TABLE A-continued

| R | Z |
|---|---|
| —N(CH₃)₂ | 3,4-bis(NH/NHCH₃)-1,2,5-thiadiazole 1-oxide |
| —N(CH₃)₂ | 3-NH-, 5-NH₂-1-methyl-1,2,4-triazole (—NH—C(=N)—N(CH₃)—N=C(NH₂)—) |
| pyrrolidin-1-yl | 3-NH-, 5-NHCH₃-1-ethyl-1,2,4-triazole |
| piperidin-1-yl | 3-NH-, 5-NHCH₃-1H-1,2,4-triazole |
| piperidin-1-yl | —CN |
| piperidin-1-yl | —C(=NSO₂NH₂)—NH₂ |
| piperidin-1-yl | —NH₂ |
| pyrrolidin-1-yl | —CN |
| pyrrolidin-1-yl | —C(=NSO₂NH₂)—NH₂ |
| pyrrolidin-1-yl | —NH₂ |
| —C(=NH)—N(CH₃)₂ | 3-NH-, 5-NH₂-1-methyl-1,2,4-triazole |
| —C(=NH)—N(pyrrolidin-1-yl) | 3-NH-, 5-NH₂-1-methyl-1,2,4-triazole |
| —C(=NH)—NHCH₃ | 3-NH-, 5-NH₂-1-methyl-1,2,4-triazole |
| —C(=NH)—N(CH₃)₂ | 3,4-bis(NH/NHCH₃)-1,2,5-thiadiazole 1-oxide |
| —C(=NH)—N(pyrrolidin-1-yl) | 3,4-bis(NH/NHCH₃)-1,2,5-thiadiazole 1-oxide |
| —C(=NH)—NHCH₃ | 3,4-bis(NH/NHCH₃)-1,2,5-thiadiazole 1-oxide |
| piperidin-1-yl | 3-NH-, 5-NH₂-1-methyl-1,2,4-triazole |

TABLE B

Structure: 2-R₁-substituted-6-(OCH₂CH₂CH₂Z)-1,2,3,4-tetrahydronaphthalene

| R₁ | Z |
|---|---|
| —N(CH₃)₂ | —NH—C(=NCN)—NHCH₃ |
| —N(CH₃)₂ | —NH—C(=CHNO₂)—NHCH₃ |
| piperidin-1-yl | 3-NH-, 5-NH₂-1-methyl-1,2,4-triazole |
| pyrrolidin-1-yl | 5-(3,4-methylenedioxybenzyl)-2-NH-pyrimidin-4(1H)-one |

4,529,723

TABLE B-continued

Structure: tetralin with $R_1$ substituent and $-OCH_2CH_2CH_2Z$ group

| $R_1$ | Z |
|---|---|
| N-morpholinyl | 5-[(6-methylpyridin-3-yl)methyl]-2-amino-pyrimidin-4(1H)-one (via —NH) |
| —NH₂ | 3,4-diamino-1,2,5-thiadiazole-1-oxide (—NH, NH₂ substituents) |
| —NHCH₃ | 3,4-diamino-1,2,5-thiadiazole-1,1-dioxide |
| —N(CH₃)₂ | 3,4-diamino-1,2,5-thiadiazole-1,1-dioxide |
| —N(CH₃)₂ | 3-amino-4-methylamino-1,2,5-thiadiazole-1-oxide |
| —N(CH₃)₂ | 5-[(6-methylpyridin-3-yl)methyl]-2-amino-pyrimidin-4(1H)-one |
| —N(Et)₂ | 5-[(1,3-benzodioxol-5-yl)methyl]-2-amino-pyrimidin-4(1H)-one |

TABLE B-continued

Structure: tetralin with $R_1$ substituent and $-OCH_2CH_2CH_2Z$ group

| $R_1$ | Z |
|---|---|
| —N(Et)₂ | 1-methyl-3,5-bis(methylamino/amino)-1,2,4-triazole type: $-NH-C(=N-N(CH_3)-)-NHCH_3$ |
| —NHEt | $-NH-C(=CHNO_2)-NH_2$ |
| —NHCH₃ | $-NH-C(=NCN)-SCH_3$ |
| 1-piperidinyl | $-NH-C(=N-CN)-NHCH_3$ |

TABLE C

Structure: indane with $R_1$ substituent and $-CH_2SCH_2CH_2Z$ group

| $R_1$ | Z |
|---|---|
| —NH₂ | $-NH-C(=NCN)-NHCH_3$ |
| —N(CH₃)₂ | $-NH-C(=NCN)-NH_2$ |
| —NHCH₃ | $-NH-C(=CHNO_2)-NHCH_3$ |
| 1-piperidinyl | $-NH-C(=CHNO_2)-NH_2$ |
| 1-pyrrolidinyl | $-NH-C(=N-CN)-S-CH_3$ |
| —NHCH₃ | 5-[(1,3-benzodioxol-5-yl)methyl]-2-amino-pyrimidin-4(1H)-one |
| 1-piperidinyl | 5-[(6-methylpyridin-3-yl)methyl]-2-amino-pyrimidin-4(1H)-one |

TABLE C-continued

Structure: indane with CH₂SCH₂CH₂Z substituent on benzene ring and R₁ on the saturated ring.

| R₁ | Z |
|---|---|
| —N(CH₃)₂ | —NH—C(=N—S(→O)—N)—NH₂ (4-amino-1,2,5-thiadiazole S-oxide) |
| pyrrolidin-1-yl | —NH—C(=N—S(→O)—N)—NHCH₃ (4-methylamino-1,2,5-thiadiazole S-oxide) |
| piperidin-1-yl | 1-methyl-3-amino-5-(NH—)-1,2,4-triazole |
| morpholin-4-yl | 1-ethyl-3-(NHCH₃)-5-(NH—)-1,2,4-triazole |
| hexahydroazepin-1-yl | 1H-3-(NHCH₃)-5-(NH—)-1,2,4-triazole |
| piperidin-1-yl | 1-ethyl-3-(NHCH₃)-5-(NH—)-1,2,4-triazole |
| pyrrolidin-1-yl | 1H-3-(NHCH₃)-5-(NH—)-1,2,4-triazole |
| —N(CH₃)₂ | 1-ethyl-3-(NHCH₃)-5-(NH—)-1,2,4-triazole |
| —C(=NH)NH₂ | 1H-3-(NHCH₃)-5-(NH—)-1,2,4-triazole |

TABLE D

Structure: indane with OCH₂CH₂CH₂Z substituent on benzene ring and R₁ on the saturated ring.

| R₁ | Z |
|---|---|
| —N(CH₃)₂ | —NH—C(=NCN)—NHCH₃ |
| pyrrolidin-1-yl | —NH—C(=CHNO₂)—NHCH₃ |
| piperidin-1-yl | 1-methyl-3-amino-5-(NH—)-1,2,4-triazole |
| morpholin-4-yl | 2-(NH—)-5-(3,4-methylenedioxybenzyl)-pyrimidin-4(1H)-one |
| —C(=NH)NH₂ | 2-(NH—)-5-[(6-methylpyridin-3-yl)methyl]-pyrimidin-4(1H)-one |
| —N(CH₃)₂ | 1-methyl-3-amino-5-(NH—)-1,2,4-triazole |
| —NH₂ | 4-amino-3-(NH—)-1,2,5-thiadiazole S-oxide |
| piperidin-1-yl | 4-amino-3-(NH—)-1,2,5-thiadiazole S,S-dioxide |

TABLE D-continued

| $R_1$ | Z |
|---|---|
| pyrrolidin-1-yl | -NH-C(=N-S(=O)_2-N)-NH_2 (4-amino-1,2,5-thiadiazole-1,1-dioxide derivative) |
| -N(CH_3)_2 | -NH-C(=N-S=O)-NHCH_3 |
| -C(=NH)-N(CH_3)_2 | 1-methyl-3-amino-5-(NH-)-1,2,4-triazole |
| -C(=NH)-N(pyrrolidinyl) | 1-methyl-3-amino-5-(NH-)-1,2,4-triazole |
| -C(=NH)-N(CH_3)_2 | 1-methyl-3-amino-5-(NH-)-1,2,4-triazole (diamino) |
| -C(=NH)-N(CH_3)_2 | -NH-C(=N-S=O)-NHCH_3 |
| -C(=NH)-N(pyrrolidinyl) | -NH-C(=N-S=O)-NHCH_3 |
| -C(=NH)-NCH_3 | -NH-C(=N-S=O)-NHCH_3 |

TABLE D-continued

| $R_1$ | Z |
|---|---|
| piperidin-1-yl | -CN |
| piperidin-1-yl | -C(=N-SO_2NH_2)-NH_2 |
| piperidin-1-yl | -NH_2 |
| pyrrolidin-1-yl | -CN |
| pyrrolidin-1-yl | -C(=N-SO_2NH_2)-NH_2 |
| pyrrolidin-1-yl | -NH_2 |

TABLE E

| $R_1$ | Z |
|---|---|
| -N(CH_3)_2 | 5-[(6-methylpyridin-3-yl)methyl]-2-amino-pyrimidin-4(1H)-one |
| -N(Et)_2 | 5-[(1,3-benzodioxol-5-yl)methyl]-2-amino-pyrimidin-4(1H)-one |

TABLE E-continued

[Structure: bicyclic with 7-membered ring fused to benzene, R₁ substituent, —CH₂SCH₂CH₂Z]

| R₁ | Z |
|---|---|
| —N(piperidine) | —NH—C(=N—N(CH₃)—N)—NHCH₃ (with N on ring) |
| —N(piperidine) | —NH—C(=CHNO₂)—NH₂ |
| —N(morpholine) | —NH—C(=NCN)—SCH₃ |
| —N(piperidine) | —NH—C(=N—CN)—NHCH₃ |

TABLE F

[Structure: tetralin (6-6 bicyclic), R₁ substituent, —CH₂SCH₂CH₂Z]

| R₁ | Z |
|---|---|
| —N(piperidine) | —CN |
| —N(piperidine) | —C(=NSO₂NH₂)—NH₂ |

TABLE F-continued

[Structure: tetralin (6-6 bicyclic), R₁ substituent, —CH₂SCH₂CH₂Z]

| R₁ | Z |
|---|---|
| —N(piperidine) | —NH₂ |
| —N(pyrrolidine) | —CN |
| —N(pyrrolidine) | —C(=NSO₂NH₂)—NH₂ |
| —N(pyrrolidine) | —NH₂ |

The compounds of this invention may be prepared by one of the following general synthetic schemes.

When the bicyclic benzenoid portion of the compound is directly attached to the X component of Formula I, these compounds may be prepared from a bicyclic phenolic (or phenylmercaptan) intermediate shown by Formula VII below.

One means of obtaining the appropriately substituted phenolic (or thiol) intermediate of Formula VII is illustrated in Scheme I. The starting material may be a bicyclic ketone having an oxy or mercaptyl substituent in any one of the four positions possible on the phenyl ring. The ketone can either be obtained from a commercially available source or prepared according to standard procedures known in the art.

The ketone is then converted to the enamine using a primary or secondary amine in the presence of acid, preferably a Lewis acid such as titanium tetrachloride. Any polar aprotic solvent may be used in this reaction, for example, toluene or methylene chloride.

The resulting enamine is reduced, preferably using a hydride reagent such as a borohydride. Sodium cyanoborohydride is one preferred reducing agent.

The phenolic protecting group is then cleaved to obtain the intermediate of Formula VII.

SCHEME I

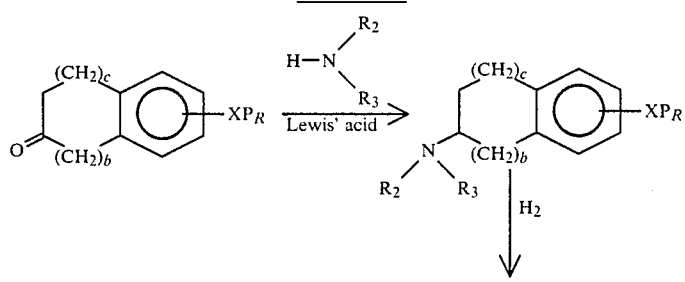

SCHEME I

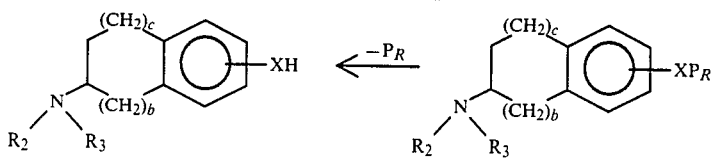

The protecting group, $P_R$, may be methyl, benzyl or the N-phthalimido alkyl. If the protecting group is chosen to be other than the N-phthalimido alkyl, the protecting group is removed according to methods known in the art. If the protecting group is N-phthalimido alkyl, then it can remain on the synthetic intermediate preceding VII and used as in the subsequent reaction step.

The formation of the ether linkage from VII is accomplished by treating the phenolic compound with a protected N-propylbromide in the presence of a base such as sodium methoxide, potassium t-butoxide or potassium carbonate. Ether coupling reagents other than a base and a bromide may also be used. (Scheme II)

Scheme II

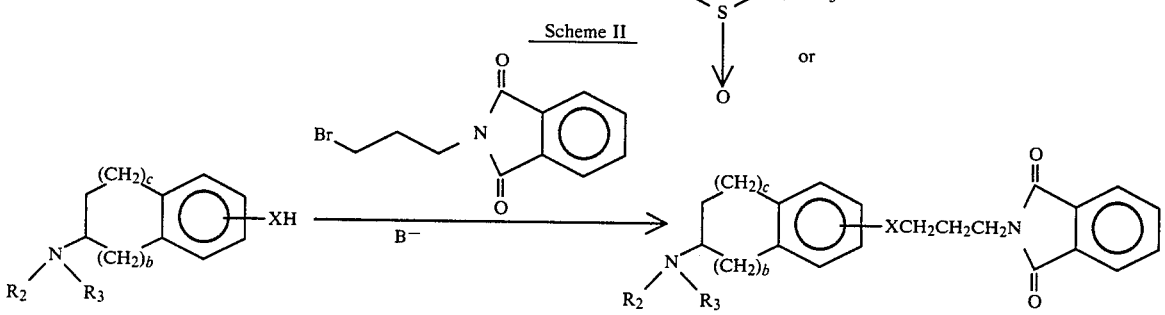

The nitrogen protecting group is preferably phthalimido but can be any protecting group insensitive to the ether formation reaction conditions, such as a base insensitive group.

The amine compound is obtained by the removal of the protecting group, for example, the phthalimido group is removed with hydrazine hydrate. (Scheme III)

Scheme III

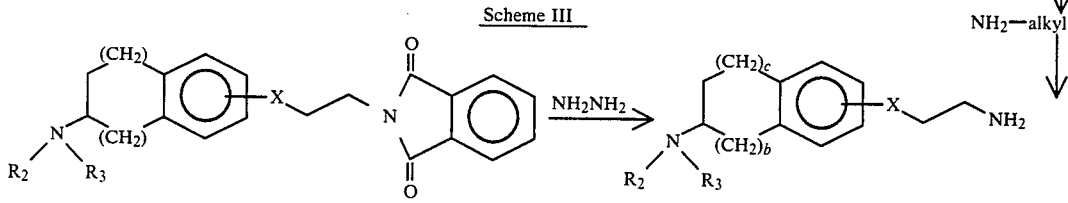

The addition of the terminal $R_4$ group comprises treating the amine with an $R_4$ end group precursor unit including those groups listed in Scheme IV. The preparation of the precursors of the $R_4$ groups and the reaction conditions under which they are coupled to the primary amine are fully described in U.S. Pat. Nos. 4,104,381, 4,279,819, 4,323,566 and GB No. 2067987A, hereby incorporated by reference.

Scheme IV

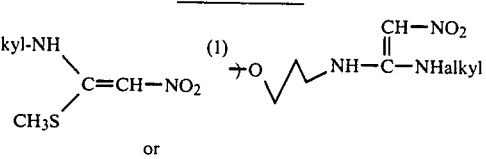

or

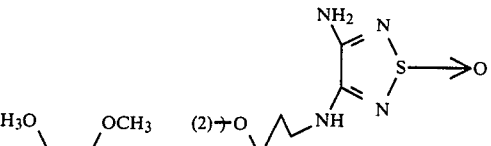

or

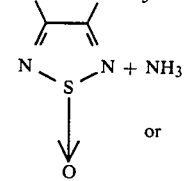

Treatment of the S-alkyl compound with a primary amine results in the N-cyano, N-alkyl guanidine analog.

Compounds within the scope of Formula I and having a methyleneoxy or methylenethioxy substituent (d=1) on the phenyl portion of the compound may be prepared by one of the reaction sequences described below.

The methyleneoxy or methylenethio ether may be prepared from the coupling of a 2-bromoethylene phthalimide in the presence of base or 2-thioethylamine, respectively, with the methylene hydroxy compound. Scheme V illustrates the formation of the methylenethio ether.

Scheme V

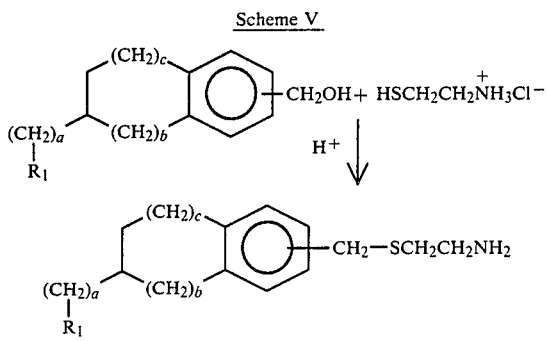

cursor such as VIII. The reduction may be conducted by hydrogenation over a rhenium catalyst, by a hydride in the presence of a Lewis acid or by acidic electrolysis and depending on choice of conditions may take place before or after the formation of the amine.

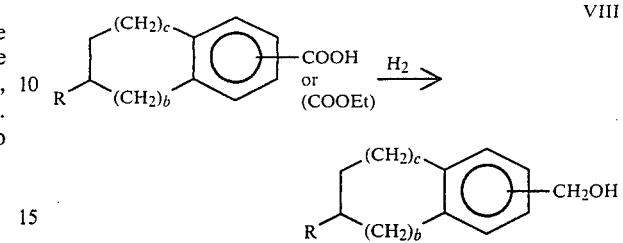

VIII

If the reduction to the methylene hydroxy compound occurs after the formation of the amine, the carboxylic acid intermediate is prepared analogously to the phenolic intermediate VII, with the acid being protected by its ester where appropriate.

Compounds within the scope of Formula I, where a is greater than zero, may be prepared by the addition of one or more carbon units at the keto-position of the starting bicyclic ketone compound as shown in Scheme VI.

Scheme VI

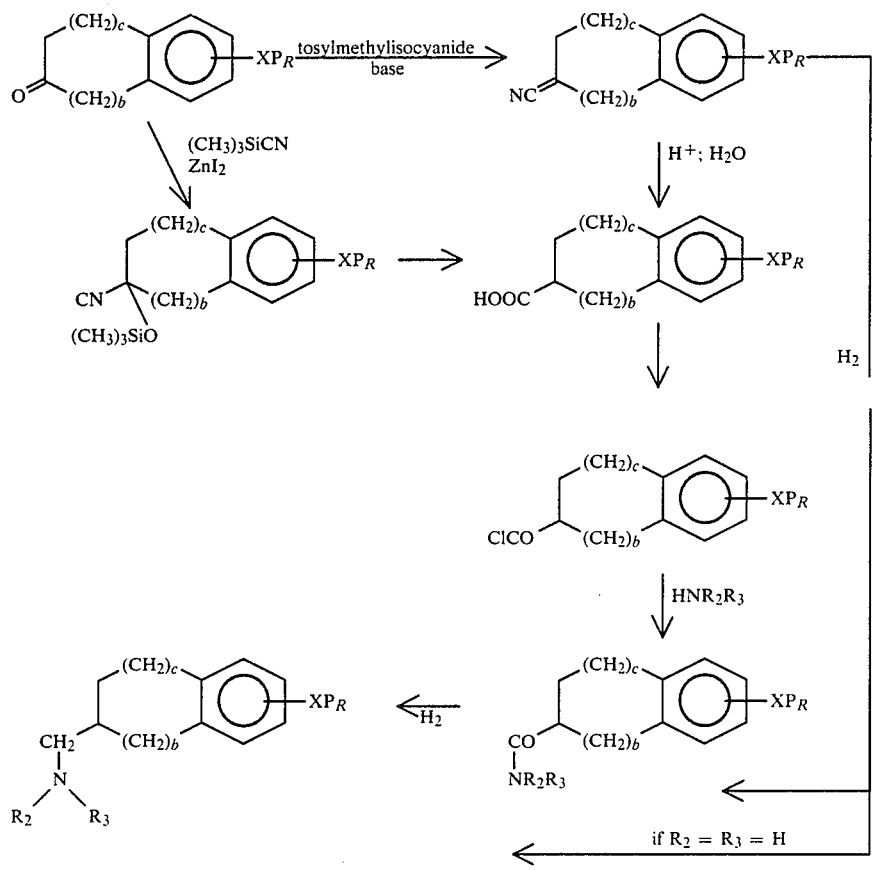

Addition of the $R_4$ group may proceed as described above in Scheme VI.

The methyleneoxy compound may be obtained by the reduction of a phenyl carboxylic acid or ester pre- Treatment of the bicylic ketone with trimethylsilylcyanide and zinc iodide forms the cyano trimethylsiloxy adduct in good yield. Treatment of the siloxy compound with a mixture of a Lewis acid such as tin$^{II}$ chloride and a concentrated halogenic acid such as conc.

HCl in glacial acetic acid results in the formation of the carboxylic acid derivative. (See, J. L. Belletire et al., *Synth. Commun.* 12, No. 10, 763–70 (19821)). An alternative pathway to the carboxylic acid compound which also provides a pathway to amido and amidino derivatives is effected by the use of tosylmethylisocyanide in the presence of base. For a complete discussion of the one-step conversion of the ketone to the cyano derivative, see O. H. Oldenziel et al., J. Org. Chem., Vol. 42, No. 19, 3114–3117 (1977). The most preferred base is tert-butoxide in a non-polar aprotic solvent such as dimethylsulfoxide or HMPT. The resulting cyano compound may be hydrolyzed to the acid by means of aqueous base, for example, aqueous sodium hydroxide, or it may be hydrolyzed to the carbamoyl derivative by acidic means including, for example, $BF_3$ in glacial acetic acid or aqueous hydrochloric acid.

The mono- or di-substituted amide may be formed by the reaction of the acyl chloride, prepared by treating the acid with $SOCl_2$ with a primary or secondary amine, i.e., $HNR_2R_3$. The amide may also be formed directly by a condensation reaction of the acid and amine or through the ester by amide-ester interchange.

Reduction of the amide results in the methylene amine. A hydride reducing agent such as $LiAlH_4$ in diethyl ether or tetrahydrofuran is preferred. Other reagents which may be used include $LiAlH_4$ and $AlCl_3$ in an ether solvent, boron tetrafluoride etherate in methylene chloride followed by sodium borohydride in ethanol, and diborane in tetrahydrofuran. These reagents may also be used to obtain the amine directly from the cyano intermediate. The preferred reagent is $LiAlH_4$. The amine obtained from the reduction of the nitrile may be alkylated to form the mono-, di- or cyclized derivative using the appropriate alkylating agent, such as an alkyl iodide, alkyl triflate or 1,4-dihalo-, 1,5-dihalo-, or 1,6-dihalo-alkyl compound. The pyrrolidinyl, piperidyl, morpholinyl and azepinyl compounds may be prepared by alkyating the amine with the appropriate reagents, for example, 1,4-dibromobutane or 1,5-dibromopentane.

The amidino derivatives may be prepared from the cyano intermediate. Treatment with anhydrous ethanolic hydrochloric acid forms the ethoxy iminium salt which forms the amidine upon treatment with a primary or secondary amine as depicted in Scheme VII.

The ethylene amino and higher alkylene amino compounds according to Formula I may be prepared via the carboxylic acid intermediate by one or more alkylene chain extending reactions as shown, for example, in Scheme VIII.

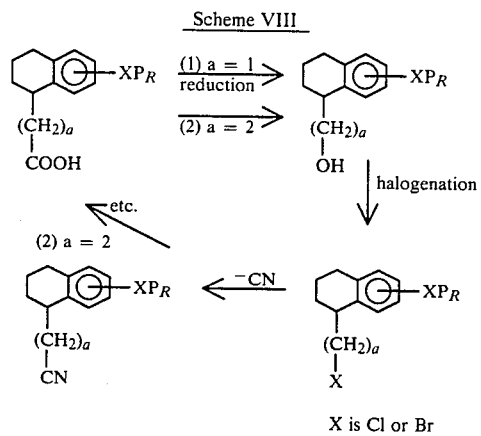

Scheme VIII

X is Cl or Br

Reduction of the carboxylic acid, shown in Scheme VIII, with a hydride such as diborane is followed by the conversion of the resultant hydroxy compound into the halo derivative with a halogenation reagent such as either $SOCl_2$ or $PBr_3$. The chain-extended cyano compound is generated by treatment of the halo derivative with cyanide and either can be converted into the amide, amine or guanidine as described above, or the chain extension process can be continued by conversion via the carboxylic acid.

When Z is $NH_2$, CN, or sulfonyl amidine, the reaction sequence is slightly modified as shown below in Scheme IX. Reaction of the phenolic intermediate with a cyano-substituted alkylating agent such as 3-cyanopropylchloride in the presence of a base produces the cyano ether compound. Reduction of the cyano group with a hydride such as lithium aluminum hydride results in the amino compound. Treatment of the cyano compound with anhydrous methanolic HCl yields an imidate intermediate which is converted to the sulfonyl amidine by treatment with sulfamide in methanol. for a complete discussion of this preparatory sequence, see U.S. Pat. No. 4,283,408, incorporated herein by reference.

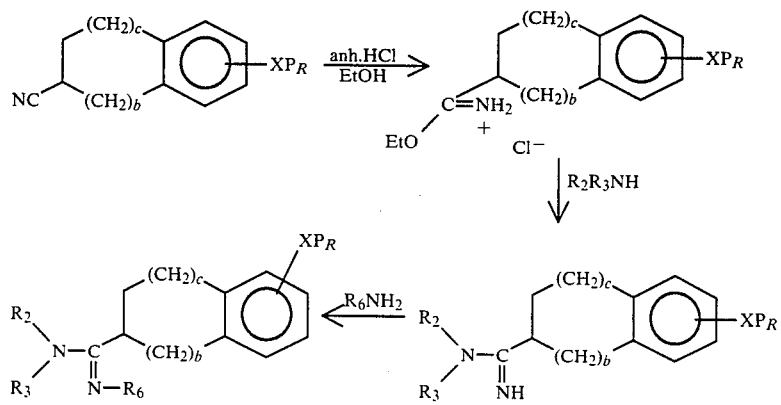

Scheme VII

Scheme IX

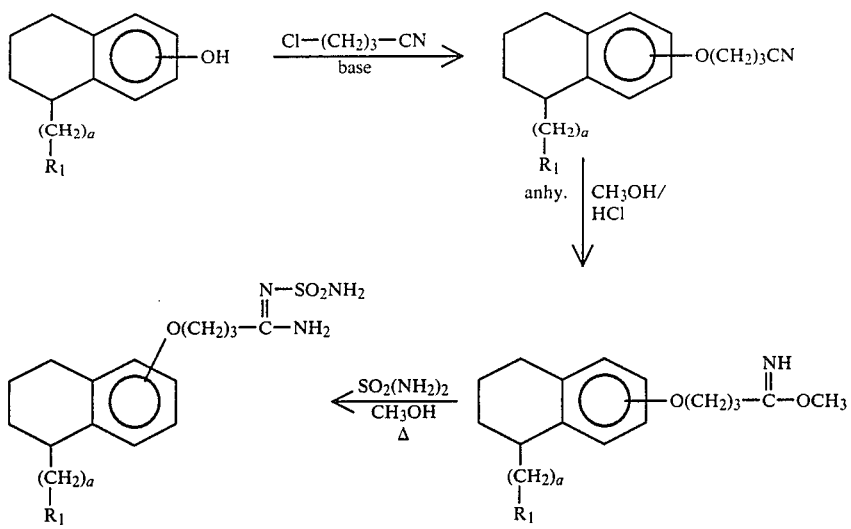

The analogous mercaptan compounds may be prepared by reacting a cyano mercaptan with the appropriate halomethylene intermediate as shown in Scheme X below. The amino sulfonyl amidine compound is prepared by reaction sequences similar to those described above.

Scheme X

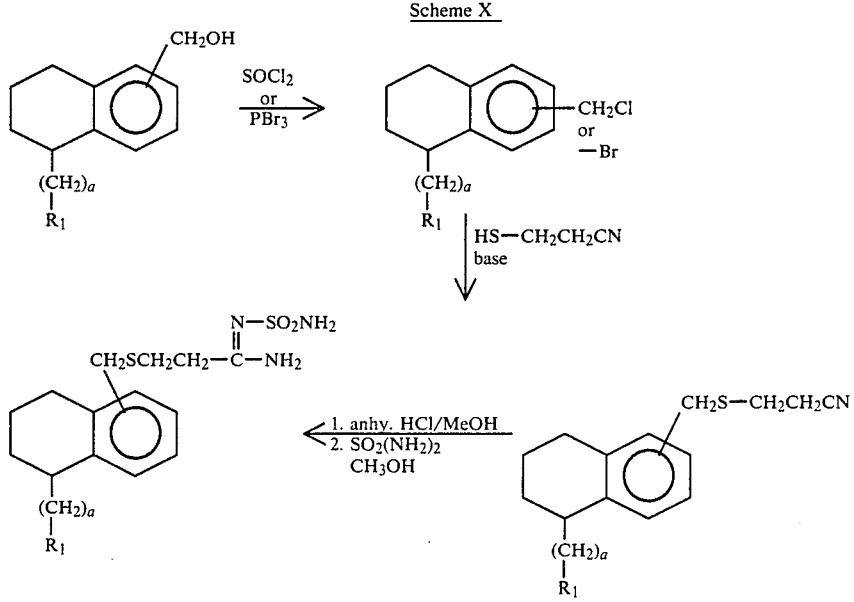

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, malic acid, oxalic acid, succinic acid, glycolic acid, lactic acid, salicylic acid, benzoic acid, nicotinic acid, phthalic acid, stearic acid, oleic acid, abietic acid, etc.

The following are selected examples of the preparation of the compounds according to this invention.

EXAMPLE 1

PREPARATION OF
3-AMINO-4-[3-[7-(1-DIMETHYLAMINO-1,2,3,4-
TETRAHYDRONAPHTHYLOXY)]-
PROPYLAMINO]-1,2,5-THIADIAZOLE-1-OXIDE

Step 1. 7-(3-Phthalimidopropoxy)-tetralone.

7-Hydroxy-1-tetralone (33.3 g) is dissolved in dimethylformamide (325 ml) and the mixture is cooled in an ice bath. Sodium methoxide (11.07 g) is added to the mixture. After the mixture is stirred for 3 min., N-(3-bromopropyl) phthalimide (54.96 g) is added to the mixture; stirring is continued and the reaction mixture stirred overnight. The resulting mixture is poured into $H_2O$ (650 ml), stirred for 1 hour, filtered, washed with $H_2O$ and air dried. The resulting fluffy near-white solid (62.8 g) is dissolved in hot ethyl acetate (600 ml), filtered while hot, rinsed with hot ethyl acetate, cooled with stirring followed by an ice bath, and filtered. The resulting solid is washed with cold ethyl acetate and air-dried to give the desired product, a fluffy white solid (M.P. 149°–150° C.)

Step 2. 1-Dimethylamino-7-(3-phthalimido)propoxy-3,4-dihydronaphthalene.

A solution of titanium tetrachloride (5.4 g) in toluene (20 ml) is added over a period of 15 minutes to a stirred solution of 7-(3-phthalimido)propoxy-1-tetralone (19.9 g) suspended in a solution of anhydrous dimethyl amine (22 g) in dry toluene (200 ml) while maintaining a reaction temperature of about 1° C. under a $N_2$ atmosphere. When the addition is complete, the reaction mixture is allowed to warm to RT and stirred at RT for 4½ hours. The reaction mixture is filtered, the salts washed with dry toluene and the clear filtrate evaporated, affording a light yellow oil, which is stored under $N_2$ and used in the next step without any further treatment.

Step 3. 1-Dimethylamino-7-(3-phthalimido)propoxy-1,2,3,4-tetrahydronaphthalene.

Anhydrous hydrogen chloride gas (3.3 g) is bubbled into a stirred reaction mixture of the phthalimido enamine obtained in the previous step in anhydrous tetrahydrofuran (210 ml) resulting in the production of a large amount of precipitate. Sodium cyanoborohydride (2.3 g) in dry methanol (50 ml) is added to the stirred suspension over a period of 5 minutes under a vigorous stream of $N_2$. When addition is complete, the reaction mixture is stirred at RT for 2½ hours, evaporated in vacuo, and the residue partitioned between ether and 2% KOH solution. The layers are separated and the aqueous layer extracted with additional ether. The combined ether layers are washed with $H_2O$ and then stirred with 5% aqueous HCl solution. The layers are separated and the aqueous acid washed with ether. The acidic layer is made strongly alkaline with 50% sodium hydroxide solution, resulting in the formation of an oily precipitate which is extracted with ether. The ether extract is washed with saturated sodium chloride solution, dried over magnesium sulfate, and evaporated in vacuo, yielding 15.9 g of a clear yellow oil. NMR analysis indicates this oil to be the desired product, which is used without further treatment for the following reaction.

Step 4. 7-(3-Aminopropoxy)-1-dimethylamino-1,2,3,4-tetrahydronaphthalene.

85% hydrazine hydrate solution (3.2 ml) is added to a solution of the phthalimido tetrahydronaphthalene (about 15 g) obtained in the preceding step dissolved in absolute ethanol (160 ml). The stirred reaction mixture is refluxed for 3 hours, after which it is allowed to cool and the resulting precipitate removed by filtration. The clear yellow filtrate is evaporated in vacuo leaving a moist yellow solid, which is triturated in 5% aqueous HCl solution. The resulting thick slurry is filtered and the clear filtrate made strongly alkaline with 50% sodium hydroxide solution, resulting in the formation of an oily precipitate. The precipitate is extracted with diethyl ether and the ether layers washed with saturated sodium chloride solution, dried over sodium sulfate, filtered and the filtrate evaporated in vacuo, yielding 7.8 g of a light amber oil. NMR and IR analysis indicate that this oil is the desired amino product, which is used without further treatment for the next reaction step.

Step 5. 3-Amino-4-[3-[7-(1-dimethylamino-1,2,3,4-tetrahydronaphthyloxy)]propylamino-1,2,5-thiadiazole-1-oxide.

3,4-Dimethoxy-1,2,5-thiadiazole-1-oxide (4.46 g) is dissolved in methanol (450 ml) and the methanolic solution cooled to 3° C. in an ice bath. 7-(3-aminopropoxy)-1-dimethylamino-1,2,3,4-tetrahydronaphthalene (7.2 g) in 75 ml methanol is slowly added to the stirred mixture and stirring continued at a constant temperature of 3° C. for one hour after addition is complete. Anhydrous ammonia (31 g) is bubbled into the reaction mixture and stirring is continued at RT for 2 hours. The reaction mixture is evaporated in vacuo and the residue triturated in ethyl acetate (75 ml), stirred in ethyl acetate for 1.5 hours, filtered, washed with ethyl acetate and diethyl ether, and dried in vacuo yielding a white powder (8.2 g), M.P. 154°–158° C., comprising more than one compound.

The powder is dissolved in a solution of 10% methanol/methylene chloride, and chromatographed on a silica gel column (250 g; 100–200 mesh) eluting the column with successively more polar solvent combinations of methanol in $CH_2Cl_2$ (10% to 60% methanol). The fractions containing the material with Rf of 0.11 are pooled and evaporated in vacuo, yielding a white solid (3.6 g), which is triturated in ether, filtered and dried, giving 3.2 g of a white powder, M.P. 160°–163° C. (dec). NMR, IR and elemental analysis indicate that this material is the desired thiadiazole-1-oxide product.

EXAMPLE 2

THE PREPARATION OF 3-AMINO-4-[3-[5-(1-DIMETHYLAMINO-1,2,3,4-TETRAHYDRONAPHTHLOXY)]-PROPYLAMINO]-1,2,5-THIADIAZOLE-1-OXIDE

Step 1. 5-[3-(N-Phthalimido)propoxy]-1-tetralone.

75.9 g of anhydrous potassium carbonate is added to a stirred solution of 5-hydroxy-1-tetralone (89.1 g) in dimethylformamide (890 ml). The reaction mixture is stirred for 15 minutes, at which time 147 g of N-(3-bromopropyl)phthalimide is added to the reaction mixture. The mixture is stirred at RT overnight. The reaction mixture is extracted with $H_2O$ and methylene chloride. The methylene chloride extracts are washed with $H_2O$, dried over sodium sulfate, filtered, and the filtrate evaporated in vacuo, yielding a dark viscous oil. The oil is dissolved in ethyl acetate, seeded, and allowed to stir at RT for two hours. The resultant solid is filtered, washed with 150 ml ethyl acetate, and allowed to air dry, yielding 72.4 g of a tan solid, M.P. 119°–121° C.

Step 2. 1-Dimethylamino-5-(phthalimido)propoxy-3,4-dihydronaphthalene.

A solution of dimethylamine (40.1 g) in dry toluene (350 ml) is added to a stirred suspension of the tetralone obtained in Step 1 (35 g) suspended in dry toluene (150 ml) under positive $N_2$ pressure. The resultant mixture is cooled in an ice bath to 1° C., followed by the addition of titanium tetrachloride (5.5 ml) in dry toluene (40 ml) over a period of 20 minutes, maintaining a temperature of <0° C. After the addition is complete, the ice bath is removed and the mixture allowed to warm to RT. After stirring for 4½ hours, the mixture is filtered, the salts washed with 400 ml dry toluene and the clear light yellow filtrate evaporated in vacuo, yielding 47 g of a slightly cloudy red-orange oil which is used in the next step without further treatment.

Step 3. 1-Dimethylamino-5-(3-phthalimido)propoxy-1,2,3,4-tetrahydronaphthalene

The dihydronaphthalene of the previous step is dissolved in 350 ml of anhydrous tetrahydrofuran and introduced into a reaction flask under $N_2$. Anhydrous hydrogen chloride (5.9 g) is passed into the stirred solution under $N_2$, followed by the addition of sodium cyanoborohydride (4.0 g) in dry methanol (100 ml) over a period of 10 minutes, resulting in a light yellow cloudy suspension. The suspension is stirred under $N_2$ at RT for about 3 hours. The reaction mixture is evaporated in vacuo at 40°–50° C., and the residue partitioned between 0.1N KOH solution and diethyl ether. The aqueous layer is extracted with ether, and the combined organic extracts washed with $H_2O$ and stirred with 5% aqueous HCl resulting in the formation of a precipitate. The solid is filtered and washed with diethyl ether and 5% HCl. The aqueous filtrate is combined with the solid and the mixture made strongly alkaline. The resultant solution is extracted with diethyl ether. The combined ether extracts are washed with saturated sodium chloride, dried over sodium sulfate, filtered and the filtrate evaporated in vacuo. The resultant viscous amber oil is identified by NMR as the desired product, which is used without further purification for the next step of the reaction sequence.

Step 4. 5-(3-Aminopropoxy)-1-dimethylamino-1,2,3,4-tetrahydronaphthalene.

4.4 ml of 99% hydrazine hydrate are added to a stirred solution of 5-(3-phthalimidopropoxy)-1-dimethylamino-1,2,3,4-tetrahydronaphthalene (26.8 g prepared in the preceding step) in absolute ethanol (270 ml). The reaction mixture is stirred and heated to reflux for 3 hours, allowed to cool, filtered and the filtrate evaporated in vacuo. The yellow residue is triturated in 5% HCl (250 ml), the suspension filtered and the solid washed with 5% HCl. The clear yellow filtrate is extracted with diethyl ether. The aqueous acidic layer is made strongly alkaline with 50% NaOH solution, resulting in an oily precipitate which is extracted with diethyl ether. The combined organic extracts are dried over sodiunm sulfate, filtered and the filtrate evaporated in vacuo, yielding 14.7 g of a light yellow oil identified by NMR as the desired 3-aminopropoxy compound.

Step 5. 3-Amino-4-[3-[5-(1-dimethylamino-1,2,3,4-tetrahydronaphthyloxy)]propylamino-1,2,5-thiadiazole-1-oxide.

7.0 g of 5-(3-aminopropoxy)-1-dimethylamino-1,2,3,4-tetrahydronaphthalene, which is obtained in the preceding step, in methanol (70 ml) is added over a period of 1 hour and 10 minutes to a solution of 3,4-dimethoxy-1,2,5-thiadiazole-1-oxide (4.57 g) in methanol (450 ml) and stirred under $N_2$ at a temperature of 2° C. for one hour. Anhydrous ammonia (26 g) is bubbled into the reaction mixture over a period of 10 minutes. The ice bath is removed and the reaction mixture allowed to warm at RT for two hours, after which the resultant mixture is evaporated in vacuo, yielding 11 g of a yellow solid. The yellow solid is suspended in absolute methanol (90 ml) and the suspension heated to boiling for 10 minutes. The cooled suspension is stirred at RT for one hour, filtered, washed with ethanol and ether, and dried at 60° C. (0.25 mm Hg) for two hours. The resultant light yellow powder has a melting point of 198°–199° C. NMR, IR and elemental analysis indicate that the solid is the desired product.

EXAMPLE 3

THE PREPARATION OF N-[3-[5-(1-DIMETHYLAMINO-1,2,3,4-TETRAHYDRONAPHTHYLOXY)]PROPYL]-N'-METHYL-2-NITRO-1,1-DIAMINOETHENE 3.58 g of 2-methylamino-2-methylthio-1-nitroethene is added to a solution of 3-[5-(1-dimethylamino-1,2,3,4-tetrahydronaphthyloxy)propylamine (6 g) in absolute ethanol (60 ml). The stirred reaction mixture is refluxed for two hours, while purging the atmosphere above the reaction mixture with $N_2$ to remove evolved methyl mercaptan. The reaction mixture is allowed to cool to RT while stirring for an additional hour. The resultant solid is filtered, washed with ethanol and ether, and dried in a vacuum dessicator at 60°–70° C. for 1½ hours, yielding 4.2 g of a near-white solid, M.P. 160°–164° C. Recrystallization from ethanol results in a white solid, M.P. 161°–165° C., with shrinkage beginning at 150° C. NMR, IR and elemental analysis indicate that this solid is the desired product.

EXAMPLE 4

THE PREPARATION OF 3-AMINO-4-[3-[5-[1-(N-PIPERIDYL)]-1,2,3,4-TETRAHYDRONAPHTHYLOXY]]PROPYLAMINO]-1,2,5-THIADIAZOLE-1-OXIDE

Step 1. 1-(N-Piperidyl)-5-(3-phthalimido)propoxy-3,4-dihydronaphthalene.

83.8 ml of piperidine are added to a stirred suspension of 5-(3-phthalimido)propoxy-1-tetralone (36.9 g) in dry toluene (370 ml) under $N_2$. The reaction mixture is stirred at RT for several minutes and then cooled in an ice bath to about 1° C. 5.8 ml of titanium tetrachloride in toluene (50 ml) is added to the reaction mixture over a period of 25 minutes, maintaining the temperature at 4°–6° C. The ice bath is removed after the addition is complete. The reaction mixture is stirred for four hours, filtered and the solid washed with dry toluene (300 ml). The filtrate is evaporated in vacuo yielding 47.6 g of a dark red-orange viscous oil. NMR indicates that this oil is the desired dihydronaphthalene product.

Step 2. 1-(N-Piperidyl)-5-(3-phthalimido)propoxy-1,2,3,4-tetrahydronaphthalene.

The red oil obtained in the previous step is dissolved in anhydrous tetrahydrofuran (350 ml) under an atmosphere of $N_2$. 5.9 g of anhydrous HCl is bubbled into the solution over a period of about two minutes, resulting in a solid precipitate. Maintaining a positive $N_2$ pressure, the suspension is stirred and 4.2 g of sodium cyanoborohydride in dry methanol (100 ml) is added over a period of 10 minutes. After the addition is complete, the reaction mixture is stirred at RT for a period of 3 hours, after which $N_2$ is bubbled vigorously through the mixture for 10 minutes. The mixture is evaporated in vacuo at 40°–45° C. and the residue partitioned between aqueous base and ether. The resulting solids are filtered away and the filtrate layers separated. The aqueous layer is washed with ether and the combined ether extracts washed with $H_2O$ and saturated sodium chloride and dried over sodium sulfate. The combined ether extracts are filtered and the filtrate evaporated in vacuo affording 38.2 g of a slightly cloudy orange oil. NMR indicates that the orange oil is the desired product, which is used without further treatment for the next step of the reaction sequence.

Step 3. 5-(3-Aminopropoxy)-1-(N-piperidyl)-1,2,3,4-tetrahydronaphthalene.

The orange oil from the preceding step is stirred with absolute ethanol (375 ml) and the ethanol supernatant decanted from the insoluble material. 6.5 ml of an 85% hydrazine hydrate solution is added to the ethanol solution and the reaction mixture refluxed for three hours. The cooled mixture is filtered and the filtrate evaporated in vacuo, yielding a yellow solid foam. The yellow solid is triturated with 5% aqueous HCl, the solids filtered away and the filtrate made strongly alkaline with sodium hydroxide solution. The resulting oily precipitate is extracted with diethyl ether and the organic extract dried over sodium sulfate. The ether solution is filtered and the filtrate evaporated in vacuo affording 21.2 g of an amber oil. Distillation of this oil in vacuo yields two fractions boiling below the range of $\leq 180°$ C. (0.5 mm Hg) to 290° C. (0.5–0.7 mm Hg). These fractions were identified as the desired end product by NMR analysis.

Step 4. 3-Amino-4-[3-[5-[1-(N-piperidyl)-1,2,3,4-tetrahydronaphthyloxy]]propylamino]-1,2,5-thiadiazole-1-oxide 5-(3-Aminopropoxy)-1-(N-piperidyl)-1,2,3,4-tetrahydronaphthalene (7.3 g), obtained in the previous step, in methanol (75 ml) is added over a period of 45 minutes to a stirred solution of 3,4-dimethoxy-1,2,5-thiadiazole-1-oxide (4.1 g) in methanol (410 ml) while maintaining a reaction temperature of 2°–3° C. under an atmosphere of $N_2$. After the addition is complete, the solution is stirred in the ice bath for 30 minutes, followed by the addition of 20.7 g of anhydrous ammonia gas bubbled into the reaction mixture over a period of five minutes. The reaction mixture is stirred at RT overnight and the resultant mixture evaporated in vacuo, resulting in 10.7 g of a foamy oil. The oil is dissolved in 10% methanol in methylene chloride (100 ml) and purified on a silica gel column (100–200 mesh; 400 g) using eluents having increasingly greater percentages of methanol. The major fractions are pooled, yielding 3.6 g of a foamy solid. The foamy solid is triturated with boiling absolute ethanol and the cooled solution is filtered. The solid is washed with ethanol and ether and dried at 65°–70° C. at 0.5 mm Hg for two hours, yielding 1.85 g of a white solid having a melting point of 204°–205° C. NMR analysis and elemental analysis identify the white solid as the desired thiadiazole oxide end product.

EXAMPLE 5

PREPARATION OF 3-AMINO-5-[3-[5-(1-DIMETHYLAMINO-1,2,3,4-TETRAHYDRONAPHTHYLOXY)]-PROPYLAMINO]-1-METHYL-1H-1,2,4-TRIAZOLE

Step 1. 5-(3-N-Phthalimidopropoxy)-1-tetralone

Potassium carbonate (94.5 g) is added to a solution of 5-hydroxy-1-tetralone (111 g) dissolved in dimethylformamide (1 liter) and the solution stirred for about 15 minutes. 183.3 g of N-(3-bromopropyl) phthalimide are added to the stirred solution, and the reaction mixture is stirred at RT overnight. The reaction mixture is partitioned between $H_2O$ and methylene chloride, and the aqueous layers extracted with methylene chloride. The combined organic layers are washed with $H_2O$ and dried over sodium sulfate. The organic extract is filtered and the filtrate evaporated in vacuo, yielding a viscous oil which is dissolved in ethyl acetate and stirred at RT for 2 hours. The resultant solid is filtered and dried in air, yielding about 90 g of a yellowish solid, M.P. 118°–121° C. NMR indicates that the solid is the desired phthalimido product.

Step 2. 1-Dimethylamino-5-(3-phthalimidopropoxy)-3,4-dihydronaphthalene.

5-(3-N-Phthalimidopropoxy)-1-tetralone (50 g) is suspended in 120 ml of anhydrous toluene. 57.4 g of dimethylamine in toluene (500 ml) are added to the stirred suspension and the mixture cooled to 1° C. A solution of titanium tetrachloride (7.92 ml) in toluene (60 ml) is added slowly to the stirred suspension, keeping the temperature below 6° C. After the addition is complete, the reaction mixture is allowed to reach RT and stirred for three hours. The reaction mixture is filtered, the filtered salts washed with dry toluene, and the filtrate evaporated in vacuo, yielding 55.7 g of a viscous yellow liquid. NMR indicates that this product is predominently the desired end product, which is used in the following step without any further treatment.

Step 3. 1-Dimethylamino-5-(3-phthalimidopropoxy)-1,2,3,4-tetrahydronaphthalene.

The viscous yellow liquid obtained in the preceding step (55.7 g) is dissolved in anhydrous tetrahydrofuran (450 ml) and anhydrous hydrogen chloride gas (5.9 g) passed through the solution. A gummy precipitate results. The reaction mixture is stirred while 5.6 g of sodium cyanoborohydride in dry methanol (120 ml) is added over a period of ten minutes, resulting in a yellow suspension. The suspension is stirred under $N_2$ at RT for 3 hours and the resultant mixture evaporated in vacuo, yielding 57.4 g of a viscous yellow liquid. The liquid is partitioned between aqueous base and diethyl ether. The aqueous layers are washed with ether and the combined ether layers washed with $H_2O$. The ether extract is stirred with 350 ml of 5% HCl and the resulting precipitate filtered and washed successively with 5% HCl and diethyl ether. The aqueous phases are made strongly alkaline and extracted with ether. The combined ether phases are washed with saturated sodium chloride and dried over sodium sulfate, filtered and evaporated in vacuo, yielding 35 g of crude product, which NMR indicates is primarily the desired tetrahydronaphthalene compound and which is used without further treatment in the next reaction step.

Step 4. 5-(3-Aminopropoxy)-1-dimethylamino-1,2,3,4-tetrahdyronaphthalene.

6.7 ml of hydrazine hydrate is added to a solution of the crude product obtained in the previous reaction step dissolved in ethanol (400 ml). The reaction mixture is stirred under reflux for 3 hours and allowed to stir at RT overnight. The reaction mixture is filtered, the filtered solid washed with ethanol, and the filtrate evaporated in vacuo, affording a yellow solid. The solid is treated with 5% HCl (250 ml), the resulting suspension filtered, and the filtrate extracted with diethyl ether. The aqueous portion is made basic, resulting in the formation of a yellow oil. The aqueous portion is extracted with diethyl ether and the combined ether extracts dried over sodium sulfate, filtered and evaporated in vacuo, yielding 17 g of a viscous yellow liquid. NMR analysis indicates that the crude product is the desired aminopropoxy tetrahydronaphthalene.

Step 5. 1-Cyano-3-[3-[5-(1-dimethylamino-1,2,3,4-tetrahydronaphthyloxy)]propyl]-2-methylpseudothiourea.

9.9 g of the amine obtained in the previous step in isopropyl alcohol (25 ml) are added over a period of ten minutes to a solution of S,S-dimethyl-N-cyanoiminodithiocarbonimidate (6.5 g) in isopropanol (100 ml). The reaction mixture is stirred at RT overnight and evaporated in vacuo, yielding a green oil. TLC and IR spectra indicate that this oil is the desired product, which is used in the next step without further treatment.

Step 6. 3-Amino-5-[3-[5-(1-dimethylamino-1,2,3,4-tetrahydronaphthyloxy)]propylamino]-1-methyl-1H-1,2,4-triazole.

4.5 g of methyl hydrazine is added to a stirred solution of the cyanopseudothiourea obtained in the preceding step (about 6 g) in dimethylformamide (60 ml). The reaction mixture is stirred for about 20 hours at a temperature of 40° C., after which it is evaporated in vacuo, yielding 13 g of a brown oil. The oil is triturated in anhydrous ether, filtered and dried, yielding 4.9 g of a green powder consisting of 2 major products. The green powder is dissolved in 10% methanol and methylene chloride and run through a silica gel column (200 g) eluting the column with successively more polar combinations of methanol and methylene chloride. The major product fractions are pooled and evaporated in vacuo, resulting in 2.6 g of a light brown solid, which is triturated in boiling acetonitrile, cooled and filtered. The solid is washed with acetonitrile and diethyl ether and dried at elevated temperature in vacuo, resulting in 1.76 g of a near-white powder, M.P. 171°–173° C. NMR, IR and elemental analysis indicate the powder to be the desired triazole product.

EXAMPLE 6

THE PREPARATION OF 2-CYANO-1-[3-[5-(1-DIMETHYLAMINO-1,2,3,4-TETRAHYDRONAPHTHYLOXY)]PROPYL]-3-METHYL GUANIDINE 10.5 g of anhydrous methylamine in absolute ethanol (75 ml) is combined with a solution of 1-cyano-3-[3-[5-(1-dimethylamino-1,2,3,4-tetrahydronaphthyloxy)]-propyl]-2-methylpseudothiourea (about 6 g) in absolute ethanol (100 ml). The reaction mixture is stirred at RT overnight while purging with $N_2$ to remove the methyl mercaptan. The reaction mixture is evaporated in vacuo, yielding 8.0 g of a dark oil, which is separated on a silica gel column (375 g), eluted with methanol in methylene chloride at increasingly greater concentrations of methanol (10% to 40%). The major pure fractions are pooled together and evaporated in vacuo, resulting in 4.1 g of a brown glass. The glass is dissolved in 50 ml of methanol and 2.1 g of O-benzoic sulfimide added to the solution. The resulting solution is evaporated in vacuo, yielding a dark oil which is triturated in anhydrous ether, the resultant solid filtered, washed with ether and allowed to air dry. The resulting solid has a melting point of 160°–165° C. The solid is dissolved in hot methanol, filtered while hot, allowed to cool, and the resultant solution diluted with an equal volume of anhydrous ether. The resultant solid is filtered, washed and methanol/diethyl ether (1:1), diethyl ether and air dried, yielding 3.5 g of a light gray solid, M.P. 171°–173° C. with shrinkage beginning at 169° C. NMR, IR and elemental analysis indicate that this solid is the desired 2-cyano guanidine saccharinate.

EXAMPLE 7

THE PREPARATION OF 3-AMINO-5-[3-[5-[1-(N-PIPERIDYL)-1,2,3,4-TETRAHYDRONAPHTHYLOXY]]-PROPYLAMINO]-1-METHYL-1H-1,2,4-TRIAZOLE

Step 1. 1-Cyano-2-methyl-3-[3-[5-[1-(N-piperidyl)-1,2,3,4-tetrahydronaphthyloxy]]propyl]-pseudothiourea.

2.9 g of 5-(3-aminopropoxy)-1-(N-piperidyl)-1,2,3,4-tetrahydronaphthylene in isopropanol (15 ml) are added over a period of 3 minutes to a stirred solution of S,S-dimethyl-N-cyanoiminodithiocarbonimidate (1.6 g) dissolved in isopropanol (20 ml). The reaction mixture is stirred at RT overnight, resulting in the formation of a solid precipitate. The solid is filtered, washed with isopropanol and diethyl ether, and dried in air and at 0.75 mm Hg, resulting in 2.9 g of a white powder, M.P. 141°–144° C. NMR and elemental analysis indicate that the white powder is the desired product.

Step 2. 3-Amino-5-[3-[5-[1-(N-piperidyl)-1,2,3,4-tetrahydronaphthyloxy]]propylamino]-1-methyl-1H-1,2,4-triazole.

Methyl hydrazine (2 ml) is added to a stirred suspension of the pseudothiourea obtained in the previous step (2.40 g) suspended in dimethylformamide (20 ml). The reaction mixture is heated and stirred at a temperature between 40°–45° C. for 24 hours. The reaction mixture is allowed to cool and evaporated in vacuo. The moist residue is triturated with anhydrous diethyl ether, the resultant solid filtered, washed with ether and allowed to air dry, yielding 1.9 g of a white powder, M.P. 160°–162° C. NMR, IR and elemental analysis indicate that this product is the desired triazole.

EXAMPLE 8

THE PREPARATION OF N-[3-[7-(1-DIMETHYLAMINO-1,2,3,4-TETRAHYDRONAPHTHYLOXY)PROPYL]-N'-METHYL-2-NITRO-1,1-DIAMINOETHENE

Step 1. 1-Dimethylamino-7-methoxy-3,4-dihydronaphthalene.

A solution of titanium tetrachloride (53.8 g, 31.2 ml) in dry toluene (200 ml) is added over a period of 45 minutes to a stirred solution of 7-methoxy-1-tetralone (100.5 g) and dimethyl amine (171 g) in dry toluene (2 l) while maintaining a reaction temperature of ≦10° C. When the addition of the titanium is complete, the ice bath is removed and the solution allowed to reach RT. The solution is stirred at RT for 3 hours. The solids are filtered, washed with dry toluene and the filtrate evaporated in vacuo, yielding 101.4 g of an amber oil which is used in the next step without further treatment.

Step 2. 7-Methoxy-1-dimethylamino-1,2,3,4-tetrahydronaphthalene.

A solution of 95% sodium cyanoborohydride (22.5 g) in methanol (500 ml) is added slowly to a stirred solution of the methoxy dihydronaphthalene of the previous step in tetrahydrofuran (1.6 l) to which has previously been added anhydrous hydrochloric acid (23.4 g). The addition is accomplished under an atmosphere of $N_2$. The reaction mixture is stirred at RT for 3 hours, $N_2$ vigorously bubbled through the reaction mixture and the mixture evaporated in vacuo, yielding a cloudy oil. The oil is taken up in 2% KOH (1 liter) and partitioned between base and diether ether. KOH pellets are added until the aqueous layer is made basic, the layers separated, and the aqueous layer washed with ether. The combined ether extracts are washed with H₂O and stirred with 5% HCl for 15 minutes. The acidic layer is washed with ether and then made basic with 50% sodium hydroxide solution. The resultant aqueous layer is extracted with ether, the ether extract dried over sodium sulfate, filtered and evaporated in vacuo, yielding about 90 g of a gold oil identified by NMR and IR as the desired tetrahydronaphthalene product.

Step 3. 7-Hydroxy-1-dimethylamino-1,2,3,4-tetrahydronaphthalene.

90 g of 7-methoxytetrahydronaphthalene obtained in the previous step are dissolved in glacial acetic acid (1 liter). 48% hydrobromic acid (1 liter) is added to the solution and the resulting reaction mixture heated to reflux for 3 hours. The reaction mixture is poured into 4 liters of H₂O and crushed ice and the solution made alkaline to pH 8 to 9. The aqueous mixture is extracted with methylene chloride. The methylene chloride extract is back-extracted with 2% KOH solution and the combined basic layers made acidic by the addition of aqueous HCl. The addition is continued until a white precipitate appears at pH about 8–9. The aqueous solution is extracted with methylene chloride and the organic layer washed with H₂O, dried, filtered and evaporated in vacuo, yielding a brown oil identified by NMR to be the desired phenol.

Step 4. 1-Dimethylamino-7-[3-(N-phthalimido)propoxy]-1,2,3,4-tetrahydronaphthalene.

Potassium t-butoxide (3.0 g) is added to a stirred solution of 1-dimethylamino-7-hydroxy-1,2,3,4-tetrahydronaphthalene (5.2 g) in dimethylformamide (50 ml). 13.2 g of N-(3-bromopropyl)phthalimide is added to the stirred reaction mixture and stirring continued for about 24 hours. The reaction is partitioned between slightly basic H₂O and diethyl ether. The layers are separated and the aqueous layer extracted with ether. The combined ether extracts are washed with 5% sodium hydroxide solution and H₂O. The ether extract is stirred with 5% aqueous hydrochloric acid solution, the layers separated and the ether extracted with additional aqueous 5% hydrochloric acid. The combined acidic aqueous layers are washed with ether and made strongly alkaline, resulting in an oily precipitate. The precipitate is extracted with diethyl ether which is washed with H₂O and saturated sodium chloride solution dried and evaporated in vacuo, yielding 4.4 g of a light yellow glassy solid. NMR analysis indicates that the solid is the desired tetrahydronaphthalene product.

Step 5. 7-(3-Aminopropoxy)-1-dimethylamino-1,2,3,4-tetrahydronaphthalene.

85% hydrazine hydrate (9.6 ml) is added to a stirred solution of the phthalimido tetrathydronaphthalene prepared as described in the previous step (about 50 g) in absolute ethanol (about 500 ml). The reaction mixture is heated at reflux for about 3 hours and allowed to cool. The resulting precipitate is removed by filtration and washed with absolute ethanol. The filtrate is evaporated in vacuo and the residue triturated with 5% aqueous hydrochloric acid. The aqueous suspension is filtered and the solid washed with 5% hydrochloric acid. The filtrate is made strongly alkaline with 50% sodium hydroxide solution, resulting in an oily precipitate which is extracted into diethyl ether. The ether extract is washed with saturated sodium chloride solution, dried, filtered and the filtrate evaporated in vacuo, yielding 28.5 g of the desired amine as an amber oil. NMR, IR and elemental analysis verify the amine structure.

Step 6. N-[3-[7-(1-Dimethylamino-1,2,3,4-tetrahydronaphthyloxy)propyl]-N'-methyl-2-nitro-1,1-diaminoethene.

1-Methylamino-1-methylthio-2-nitroethene (3.58 g) is added to a solution of the tetrahydronaphthyloxy amine prepared in the preceding step (6.0 g) in absolute ethanol (60 ml). The reaction mixture is heated to reflux for about 2 hours while purging the reaction mixture with N₂. The mixture is allowed to cool and the resultant solid filtered, washed with diethyl ether and dried, yielding about 2.9 g of a white solid. The filtrate is evaporated in vacuo and the residue dissolved in hot absolute ethanol. Diethyl ether is added, resulting in the formation of a solid which is filtered and dried, giving 1.4 g of a white solid, M.P. 148°–152° C. The two solids are combined and dissolved in boiling isopropyl alcohol, allowed to cool, filtered, washed with isopropyl alcohol and ether, and dried under vacuum. The resulting white powder (2.7 g) has a melting point of 153°–157° C. NMR and elemental analysis identify the solid as the desired diaminoethene product.

EXAMPLE 9

THE PREPARATION OF 3-AMINO-5-[3-[7-(1-DIMETHYLAMINO-1,2,3,4-TETRAHYDRONAPHTHYLOXY)]-PROPYLAMINO]-1-METHYL-1H-1,2,4-TRIAZOLE

Step 1. 7-(3-N-Phthalimidopropoxy)-1-tetralone.

Sodium methoxide (19.8 g) is added to a cooled, stirred solution of 7-hydroxy-1-tetralone (59.5 g) dissolved in dimethylformamide (600 ml). After addition is complete and reaction mixture is stirred for 3 minutes, N-(3-bromopropyl)phthalimide (98.3 g) is added and the reaction mixture stirred overnight. The reaction mixture is poured into H₂O and stirred for an hour, filtered, the solid washed with H₂O and dried in air to give 134 g of a brown solid. The brown solid is recrystallized from hot ethyl acetate, yielding 43.5 g of a white fluffy solid, M.P. 148°–150° C. NMR identifies the recrystallized product as the desired phthalimide.

Step 2. 1-Dimethylamino-7-(3-N-phthalimidopropoxy)-3,4-dihydronaphthalene.

7-(3-N-Phthalimidopropoxy)-1-tetralone (93.5 g) is suspended in a solution of dimethyl amine (101.3 g) in toluene (1 liter) under N₂. The stirred suspension is cooled to about 1° C. and titanium tetrachloride (14.6 ml, 25.2 g) in toluene (100 ml) is added to the stirred suspension over a period of 45 minutes, keeping the temperature below 7° C. After addition is complete, the reaction mixture is allowed to reach RT and stirred for 4½ hours. The reaction mixture is filtered and the filtered solid washed with dry toluene. The toluene filtrate is evaporated in vacuo, yielding about 100 g of a yellow oily liquid, identified by NMR as the desired product.

Step 3. 1-Dimethylamino-7-(3-N-phthalimidopropoxy)-1,2,3,4-tetrahydronaphthalene.

Sodium cyanoborohydride (10.2 g) in dry methanol (150 ml) is added slowly with stirring to a solution of the phthalimido dihydronaphthalene prepared in the preceding step (about 100 g) in anhydrous tetrahydrofuran (550 ml) in which 16 g of anhydrous hydrogen chloride is dissolved. At the end of the addition, the reaction mixture comprises a fine suspension and is stirred at RT for 3 hours under N₂. The reaction mixture is evaporated in vacuo, resulting in a viscous liquid which is partitioned between 5% potassium hydroxide solution and diethyl ether. The layers are separated and the basic layer washed with ether. The ether extracts are combined and stirred with 5% HCl. The aqueous layer is washed with ether and then made strongly basic with 50% sodium hydroxide solution. The basic aqueous extract is washed with ether and the ether extract washed with sodium chloride, dried, filtered and the ether solution evaporated in vacuo to yield a pale yellow solid. NMR indicates that this solid is the desired tetrahydronaphthalene product.

Step 4. 1-Dimethylamino-7-(3-aminopropoxy)-1,2,3,4-tetrahydronaphthalene.

Hydrazine hydrate (3.56 g) is added to a solution of the tetrahydronaphthalene obtained in the preceding step dissolved in 180 ml of absolute ethanol. The reaction mixture is stirred and heated to reflux for 3 hours. The resultant solid is filtered and the filtrate evaporated in vacuo, yielding a pale yellow solid. The solid is triturated with 5% HCl, the resultant thick slurry filtered, and the solid washed with 5% HCl. The acidic phase is made strongly basic with sodium hydroxide solution until a gold oil appears. The solution is extracted with ether, the ether washed with saturated sodium chloride solution and dried over sodium sulfate. The sodium sulfate is filtered and the ether evaporated in vacuo, resulting in the desired amine product as a viscous oil.

Step 5. 1-Cyano-3-[3-[7-(1-dimethylamino-1,2,3,4-tetrahydronaphthyloxy)]propyl]-2-methylpseudothiourea.

The amine obtained in the preceding step (8.6 g) dissolved in isopropanol (35 ml) is added over a period of one minute to a stirred solution of S,S-dimethyl-N-cyanoiminodithiocarbonimidate (5.6 g) dissolved in 70 ml of isopropanol. The reaction mixture is stirred at RT overnight and then evaporated in vacuo, yielding 13.6 g of the desired cyano product as a viscous amber oil.

Step 6. 3-Amino-5-[3-[7-(1-dimethylamino-1,2,3,4-tetrahydronaphthyloxy)]propylamino]-1-methyl-1H-1,2,4-triazole.

Methyl hydrazine (11 ml) is added to a stirred solution of the cyanotetrahydronaphthalene obtained in the previous step (about 10 g) dissolved in dimethylformamide (110 ml). The reaction mixture is stirred at about 40° C. for 24 hours, and evaporated under vacuum resulting in a residue of amber oil (16.2 g). The oil is separated on a silica gel column (290 g; 70-230 mesh) using as eluent methanol in methylene chloride ranging from 10% methanol to 30% methanol. The major fractions are pooled and evaporated in vacuo, resulting in 6.7 g of a viscous amber oil. The oil is triturated in anhydrous ether, resulting in the formation of a solid which is filtered, washed with ether and dried, resulting in 5.4 g of a near-white solid, M.P. 120°-125° C. This solid is recrystalized from hot acetonitrile and dried under vacuum, resulting in 3.5 g of a near-white powder, M.P. 127°-130° C. NMR, IR and elemental analysis indicate the solid as the desired triazole product.

EXAMPLE 10

THE PREPARATION OF 3-AMINO-4-[3-[6-(1-DIMETHYLAMINO-1,2,3,4-TETRAHYDRONAPHTHYLOXY)]-PROPYLAMINO]-1,2,5-THIADIAZOLE-1-OXIDE

Step 1. 6-(3-N-Phthalimidopropoxy)-1-tetralone.

77.5 g of N-bromopropylphthalimide are added to a stirred solution of 6-hydroxy-1-tetralone (48.6 g) and potassium carbonate (39.9 g) in dimethylformamide (480 ml). The reaction mixture is stirred at RT overnight, and then poured into a stirred mixture of $H_2O$ and methylene chloride. The layers are separated and the aqueous portion washed with methylene chloride. The combined methylene chloride fractions are washed with $H_2O$, dried over sodium sulfate, filtered and the filtrate evaporated in vacuo, yielding an off-white solid which is recrystallized from absolute ethanol, yielding 73.1 g of crystals, M.P. 143°-145° C.

Step 2. 1-Dimethylamino-6-(3-N-phthalimidopropoxy)-3,4-dihydronaphthalene.

Dimethylamine (81.6 g) in dry toluene (600 ml) is added to a stirred suspension of 6-(3-N-phthalimidopropoxy)-1-tetralone (71.3 g) in dry toluene (200 ml) kept at a temperature of 0° C. under $N_2$. Titanium tetrachloride (19.3 g, 11.2 ml) in dry toluene (80 ml) is added slowly to the stirred suspension, keeping the temperature of the reaction mixture below 10° C. The reaction mixture is stirred under $N_2$ overnight, after which it is filtered, the salts washed with dry toluene and the filtrate evaporated in vacuo, yielding 85.9 g of a yellow viscous liquid used as is in the next step without further purification.

Step 3. 1-Dimethylamino-6-(3-N-phthalimidopropoxy)-1,2,3,4-tetrahydronaphthalene.

Sodium cyanoborohydride (9.26 g of 95%) in dry methanol (220 ml) is added slowly to a vigorously stirred mixture of the dihydronaphthalene obtained in the previous step (85.9 g) dissolved in tetrahydrofuran (600 ml) in which anhydrous hydrogen chloride (15 g) has been dissolved. The reaction mixture is stirred at RT overnight under $N_2$. Another 200 ml of methanol is added to the reaction mixture and nitrogen gas bubbled through the mixture for 10 minutes. The resulting solution is evaporated in vacuo, yielding a brown oil which is partitioned between aqueous base and diethyl ether. The aqueous layer is washed with ether and the combined ether portions washed with $H_2O$ and stirred with aqueous 5% HCl. The resultant precipitate is filtered and combined with the separated aqueous layer. The aqueous layer is made alkaline and extracted with ether, and the combined ether portions are washed with saturated sodium chloride and $H_2O$, dried over sodium sulfate and filtered. The filtrate is evaporated, resulting in 52 g of a viscous yellow liquid. NMR analysis indicates that the yellow liquid is the desired tetrahydronaphthalene.

Step 4. 1-Dimethylamino-(3-aminopropoxy)-1,2,3,4-tetrahydronaphthalene.

80% hydrazine hydrate (10.0 ml) is added to a stirred solution of the phthalimido tetrahydronaphthalene obtained in the previous step (52 g) dissolved in absolute ethanol (500 ml). The reaction mixture is refluxed for 3 hours, allowed to cool, and the resultant solid filtered and the filtrate evaporated in vacuo. The yellow solid residue is triturated with aqueous 5% HCl, filtered, washed with aqueous HCl, and the filtrate extracted with ether. The acidic aqueous portion is made basic with 50% sodium hydroxide. The resultant diphasic mixture is extracted with ether, the ether extracts dried, filtered, and evaporated, yielding a yellow viscous liquid (30.1 g). The liquid is dried under high vacuum, yielding 27.7 g of the crude product, which is used as is in the next step.

Step 5. 3-Amino-4-[3-[6-(1-dimethylamino-1,2,3,4-tetrahydronaphthyloxy)]propylamino]-1,2,5-thiadiazole-1-oxide 1-Dimethylamino-(3-aminopropoxy)-1,2,3,4-tetrahydronaphthalene (7.0 g) in methanol (70 ml) is added over a period of 1 hour to a stirred solution of 3,4-dimethoxy-1,2,5-thiadiazole-1-oxide (4.57 g) in methanol (450 ml) cooled to a temperature of 2° C. under $N_2$. Anhydrous ammonia (30 g) is bubbled over a period of 10 minutes into the reaction mixture and the solution stirred at RT overnight. The reaction mixture is evaporated in vacuo, yielding a yellow solid (10.4 g). The solid is dissolved in 10% methanol and methylene chloride mixed with Celite and filtered. The cloudy filtrate is evaporated in vacuo, yielding a glass which is chromatographed on a column of silica gel (350 g) eluting the column with methanol in methylene chloride ranging from a methanol percentage of 10% to 60% methanol. The fractions having an Rf of 0.07 are pooled and evaporated in vacuo, yielding 3.5 g of a dark oil. The oil is triturated in ether, the solid filtered, washed with ether and dried in high vacuum, giving 2.76 g of a near-white powder, M.P. 149°–152° C. The powder is dissolved in hot absolute ethanol and ether, the gummy precipitate filtered, and the filtrate evaporated in vacuo, triturated in ether, filtered, and the solid dried under high vacuum, giving 2.1 g of a near-white powder, M.P. 157°–159° C. (dec). NMR, IR and elemental analysis indicate the desired product.

EXAMPLE 11

PREPARATION OF 3-AMINO-4-[3-[5-[[1-(N-MORPHOLINYL)]-1,2,3,4-TETRAHYDRONAPHTHYLOXY]PROPYLAMINO]-1,2,5-THIADIAZOLE-1-OXIDE

Step 1. 5-Methoxy-(1-(N-morpholinyl))-3,4-dihydronaphthalene.

Titanium tetrachloride (15.2 g) in dry toluene (105 ml) is added slowly to a stirred solution of 5-methoxy-1-tetralone (49 g), and morpholine (160 g) in dry toluene (1 l) cooled in an ice bath to a temperature of 3° C. under a nitrogen atmosphere. The reaction mixture is allowed to warm to RT and stirred at RT under $N_2$ overnight. The reaction mixture is filtered, the filtered solid washed with dry toluene and dry THF and the combined filtrates evaporated in vacuo to a yellow solid (63.5 g), M.P. 80°–90° C.

Step 2. 5-Methoxy-1-(N-morpholinyl)-1,2,3,4-tetrahydronaphthalene.

95% sodium cyanoborohydride (10.2 g) in methanol (225 ml) is added to a stirred reaction mixture of the 5-methoxy dihydronaphthalene obtained in the previous step (about 63 g) and 11.7 g of anhydrous hydrochloric acid dissolved in anhydrous tetrahydrofuran (1 liter). The reaction mixture is stirred at RT for 3 hours, $N_2$ gas vigorously bubbled through the reaction mixture and the resulting suspension evaporated in vacuo, yielding a whitish solid. The solid residue is partitioned between aqueous base and methylene chloride, the alkaline layer washed with methylene chloride and the combined methylene chloride portions washed with $H_2O$. The methylene chloride extract is stirred with aqueous 5% HCl, the layers separated and the organic layer again washed with aqueous 5% HCl. The aqueous layer is made extremely basic with 50% sodium hydroxide solution and the basic solution extracted with methylene chloride. The methylene chloride extract is washed with $H_2O$, dried, filtered, and the filtrate evaporated in vacuo, yielding 18.3 g of an oil which later solidifies. NMR analysis indicates that the crude product is the desired compound, which is used without further treatment in the next synthetic step.

Step 3. 5-Hydroxy-1-morpholinyl-1,2,3,4-tetrahydronaphthalene.

48% hydrobromic acid (180 ml) is added to a stirred solution of the crude tetrahydronaphthalene obtained in the previous step (18.3 g) dissolved in glacial acetic acid (180 ml) under an atmosphere of $N_2$. The reaction mixture is refluxed under $N_2$ for 3 hours, after which it is poured into crushed ice, resulting in the formation of a green precipitate. The precipitate is filtered and the filtrate extracted with ether. The aqueous layer is made basic (pH 8–9) forming a white precipitate. The precipitate is extracted with ether, the layers separated, and the ether portion washed with $H_2O$, dried over sodium sulfate, filtered and evaporated in vacuo, resulting in a white crystalline solid (14.9 g), M.P. 194°–196° C. NMR indicates the desired phenolic product.

Step 4. 5-(3-Phthalimidopropoxy)-1-(N-morpholinyl)-1,2,3,4-tetrahydronaphthalene.

Potassium t-butoxide (7.8 g) is added to a stirred solution of 5-hydroxy-1-morpholinyl-1,2,3,4-tetrahydronaphthalene (14.7 g) dissolved in dimethylformamide (150 ml) and the reaction solution stirred for a few minutes. N-(3-bromopropyl)phthalimide (33.8 g) is added to the reaction mixture and stirring is continued at RT for 2 days. The reaction mixture is partitioned between $H_2O$ and ether, the layers separated and the aqueous layer adjusted to a pH>10 with sodium hydroxide solution and extracted with additional diethyl ether. The combined ether layers are washed with $H_2O$ and aqueous 5% hydrochloride acid. The acidic aqueous extracts are made strongly alkaline with sodium hydroxide solution, resulting in an oily precipitate which is extracted with ether and methylene chloride. The combined organic layers are washed with 5% aqueous sodium hydroxide and saturated sodium chloride, dried over sodium sulfate, filtered, and evaporated, resulting in 22.6 g of an amber oil as the crude product used in the next step.

Step 5. 5-(3-Aminopropoxy)-1-(N-morpholinyl)-1,2,3,4-tetrahydronaphthalene.

85% hydrazine hydrate (3.3 ml) is added to a suspension of the phthalimido tetrahydronaphthalene obtained in the preceding step (21.9 g) in absolute ethanol (200 ml). The reaction mixture is heated to reflux with stirring for 3½ hours, after which the reaction mixture is allowed to cool, filtered and the solid washed with ethanol. The ethanol filtrate is evaporated in vacuo, yielding 3.4 g of a solid. The solid and residue are combined and stirred with 5% aqueous HCl, the mixture filtered and the solid washed with 5% HCl. The filtrate is made strongly alkaline with 50% sodium hydroxide solution, resulting in the formation of an oily precipitate which is extracted with methylene chloride. The methylene chloride extract is washed with saturated sodium chloride solution, dried over sodium sulfate, filtered and evaporated in vacuo, yielding 13.2 g of an amber oil which is identified by NMR analysis to be the desired amine product.

Step 6. 3-Amino-4-[3-[5-[1-(N-morpholinyl)-1,2,3,4-tetrahydronaphthyloxy]]propylamino]-1,2,5-thiadiazole-1-oxide 5-(3-Aminopropoxy)-1-(N-morpholinyl)-1,2,3,4-tetrahydronaphthalene (6.3 g) in methanol (60 ml) is added over a period of one hour to a stirred solution of 3,4-dimethoxy-1,2,5-thiadiazole-1-oxide (3.35 g) in methanol (350 ml), cooled in an ice bath under an atmosphere of N₂. The reaction mixture is stirred in an ice bath for 2½ hours, followed by the addition of anhydrous ammonia (25.0 g) bubbled into the reaction mixture over a period of 10 minutes. The solution is stirred at RT for 2 hours, after which the reaction mixture is evaporated in vacuo, resulting in 9.3 g of a solid. The solid is ground into a powder and suspended in absolute ethanol. The suspension heated to boiling, cooled, and the cooled suspension filtered. The solid is washed with ethanol and ether, and dried under vacuum, giving 4.8 g of a white solid, M.P. 198°–200° C. (dec). NMR and elemental analysis establish this solid as the desired triazole product.

EXAMPLE 12

PREPARATION OF 3-AMINO-5-[3-[5-[[1-(N-MORPHOLINYL)]-1,2,3,4-TETRAHYDRONAPHTHYLOXY]]-PROPYLAMINO]-1-METHYL-1H-1,2,4-TRIAZOLE

A mixture of 5-(3-aminopropoxy)-1-(N-morpholinyl)-1,2,3,4-tetrahydronaphthalene (5.2 g) and the methyl ester of N-cyano-1-methyl-2-(phenylmethylene)hydrazinecarboxyimidothioic acid (4.0 g) is heated neat to a temperature of 70° C. in a vacuum of 15 mm Hg for a period of 4½ hours. The resultant neat mixture is cooled and triturated in acetone, resulting in a solid precipitate. The addition of 5% aqueous hydrochloric acid affords a clear light-green solution which is stirred at RT for an hour, diluted with H₂O and washed with diethyl ether. The aqueous solution is made strongly alkaline with 50% sodium hydroxide solution resulting in an oily precipitate, which is extracted with ethyl acetate. The ethyl acetate extract is washed with saturated sodium chloride, dried over sodium sulfate, filtered and the filtrate evaporated in vacuo, resulting in 6.9 g of a viscous amber oil. The oil is dissolved in hot acetonitrile, filtered, the acetonitrile solution allowed to cool, and the resultant precipitate filtered, yielding 3.38 g of a solid, M.P. 150°–153° C. NMR, IR and elemental analysis indicate the solid to be the desired triazole product.

EXAMPLE 13

PREPARATION OF 3-AMINO-4-[3-[5-(1-PYRROLIDINYL-1,2,3,4-TETRAHYDRONAPHTHYLOXY)]PROPYLAMINO]-1,2,5-THIADIAZOLE-1-OXIDE

Step 1. 5-Methoxy-1-pyrrolidinyl-3,4-dihydronaphthalene.

Titanium tetrachloride (31.1 ml) in dry toluene (210 ml) is added slowly to a stirred solution of 5-methoxy-1-tetralone (100 g) and pyrrolidine (263 g) in anhydrous toluene (2 l) cooled in a methanol ice bath under N₂ while maintaining a temperature of less than 7° C. When the addition is complete, the reaction mixture is allowed to stir at RT for 3½ hrs. The reaction mixture is filtered, the solid washed with anhydrous toluene, and the filtrate evaporated in vacuo, resulting in a gold viscous liquid, which is dissolved in 1.8 l of dry tetrahydrofuran and filtered. The filtrate is used as is in the next step.

Step 2. 5-Methoxy-1-pyrrolidinyl-1,2,3,4-tetrahydronaphthalene.

Anhydrous hydrochloric acid in methanol (23 g) is added to the filtrate obtained in the previous step, while stirring the mixture under N₂. Sodium cyanoborohydride (22.7 g) in methanol (180 ml) is added slowly to the reaction mixture with vigorous stirring. The resultant suspension is stirred under N₂ for almost 3 hrs at RT, nitrogen gas is bubbled through the solution and the solution evaporated in vacuo. The resultant viscous liquid is taken up in aqueous base and diethyl ether. The aqueous layer is made strongly basic with solid potassium hydroxide and the layers separated. The aqueous layer is washed with ether and the ether portions combined and stirred with 5% aqueous hydrochloric acid solution. The ether portion is separated and washed with additional hydrochloric acid solution. The combined aqueous portions are made alkaline, resulting in the formation of an immiscible liquid which is extracted with ether. The ether extract is washed with H₂O, dried and evaporated in vacuo, resulting in a solid identified as the desired material. The solid is used in the next step without purification.

Step 3. 5-Hydroxy-1-pyrrolidinyl-1,2,3,4-tetrahydronaphthalene.

48% hydrobromic acid (1 l) is added to a stirred solution of the methoxy tetrahydronaphthalene obtained in the previous step dissolved in glacial acetic acid (1 l) under an atmosphere of nitrogen. The reaction mixture is heated to reflux for 2 hrs, then poured into H₂O/crushed ice and sodium hydroxide pellets added until a white solid appears. Aqueous base is used to adjust the pH to about 8 to 9. The mixture is filtered, and the filtered solid is ground and suspended in H₂O and filtered again. The solid is recrystallized from ethyl acetate, yielding a whitish solid, M.P. 151°–153° C. NMR analysis indicates that the product is the desired 5-hydroxy-tetrahydronaphthalene.

Step 4. 5-(3-N-Phthalimidopropoxy)-1-N-pyrrolidinyl-1,2,3,4-tetrahydronaphthalene.

Potassium t-butoxide (30.9 g) is added to a solution of 5-hydroxy-1-(N-pyrrolidinyl)-1,2,3,4-tetrahydronaphthalene (65.3 g) in dimethylformamide (650 ml). The reaction mixture is stirred for 5 minutes, after which N-(3-bromopropyl)phthalimide (134.5 g) is added to the reaction mixture. Stirring is continued over the weekend. The reaction mixture is diluted with H₂O and extracted with ether. The aqueous portion is made basic with 50% sodium hydroxide solution and again extracted with ether. The combined ether extracts are washed with H₂O, stirred with 5% sodium hydroxide solution, the basic layers back-extracted with ether and the combined ether extracts washed with H₂O and stirred with 5% aqueous hydrochloric acid solution. The layers are separated and the ether washed with 5% aqueous hydrochloric acid solution and the combined aqueous acid extracts made alkaline with 50% sodium hydroxide solution, resulting in a white precipitate. The precipitate is extracted with ether and methylene chloride and the aqueous portion extracted with methylene chloride. The combined organic extracts are dried, filtered and evaporated in vacuo, resulting in 67.1 g of a pinkish solid. The solid is recrystallized from ethanol, filtered, dried in vacuo, yielding about 51 g of dry product, which is used without further purification in the next step.

Step 5. 5-(3-Aminopropoxy)-1-(N-pyrrolidinyl)-1,2,3,4-tetrahydronaphthalene.

85% hydrazine hydrate (8.3 ml) is added to a stirred solution of the phthalimido pyrrolidinyl tetrahydronaphthalene obtained in the previous step (about 51 g) dissolved in absolute ethanol (500 ml), and the reaction mixture is heated to reflux for 3 hours and then allowed to cool. A precipitate forms upon cooling, and the reaction mixture is filtered, the precipitate washed with absolute ethanol, and the filtrate evaporated in vacuo, resulting in a solid. The solid is triturated with 5% aqueous HCl, filtered, and the solid washed with additional 5% HCl solution. The acidic filtrate is washed with diethyl ether and made basic with 50% aqueous sodium hydroxide, resulting in the formation of a golden oil. The oil is extracted with diethyl ether, washed with H₂O, dried over sodium sulfate, filtered and evaporated in vacuo, resulting in 17 g of a golden oil. NMR analysis indicates that this oil is the desired amino product.

Step 6. 3-Amino-4-[3-[5-(1-pyrrolidinyl-1,2,3,4-tetrahydronaphthyloxy)]propylamino]-1,2,5-thiadiazole-1-oxide.

5-(3-Aminopropoxy)-1-(N-pyrrolidinyl)-1,2,3,4-tetrahydronaphthalene (7.0 g) in methanol (100 ml) is added over a period of 90 minutes to a stirred solution of 3,4-dimethoxy-1,2,5-thiadiazole-1-oxide (4.14 g) in methanol (450 ml), while maintaining the temperature at less than 3° C. The reaction mixture is stirred for an additional 1½ hours, after which anhydrous ammonia is bubbled into the reaction mixture over a period of 10 minutes. The reaction mixture is stirred at ambient temperature overnight, evaporated in vacuo, yielding 9.9 g of an off-white solid. The solid is triturated with ethyl acetate, filtered, and the solid dissolved in 10% methanol in methylene chloride. The methanolic solution is placed on a silica gel column (silica gel: Kiesel gel 60, 70–230 mesh) and eluted with successively higher concentrations of methanol in methylene chloride ranging from 10 to 30%. The major fractions are pooled together and evaporated in vacuo, yielding 6.5 g of a solid which is recrystallized from ethanol, yielding 3 g of a yellow solid, M.P. 184°–186° C. NMR, IR and elemental analysis indicate the desired thiadiazole-1-oxide product.

EXAMPLE 14

PREPARATION OF 3-AMINO-4-[3-[6-(1-DIMETHYLAMINOINDANYLOXY)]PROPYLAMINO]-1,2,5-THIADIAZOLE-1-OXIDE

Step 1. 1-Dimethylamino-6-methoxy-1,2-indene.

Titanium tetrachloride (11.5 g) in toluene (50 ml) is added over a period of 20 minutes to a stirred solution of 6-methoxy-1-indanone (19.6 g), anhydrous dimethylamine (32 g) in anhydrous toluene (350 ml) under an atmosphere of N₂, while maintaining a temperature of less than 9° C. After the addition is complete, the reaction mixture is a light green slurry, which is stirred at RT for 3 hours, filtered, and the filtrate evaporated in vacuo, yielding 23.2 of a green oil. NMR indicates that 80–85% of the oil is the desired eneamine, which is used without further treatment in the next step.

Step 2. 1-Dimethylamino-6-methoxy indan.

A solution of anhydrous HCl (4.3 g) in THF (40 ml) is added to a stirred solution of the indene obtained in the previous step (23.0 g) in anhydrous THF (350 ml) under an atmosphere of N₂. Sodium cyanoborohydride (4.32 g) in methanol (75 ml) is added to the stirred reaction mixture over a period of 15 minutes, and the reaction mixture is stirred at RT under N₂ for an additional 4 hours. Nitrogen is vigorously bubbled through the reaction mixture for several minutes, after which it is evaporated in vacuo and the residue partitioned between methylene chloride and aqueous base. The layers are separated and the aqueous layer extracted with methylene chloride. The combined methylene chloride fractions are washed with H₂O and stirred with 5% aqueous HCl. The combined acidic aqueous fractions are washed with methylene chloride and then made strongly alkaline with 50% sodium hydroxide solution, resulting in an oily precipitate. The precipitate is extracted with methylene chloride and the methylene chloride extract washed with saturated sodium chloride, dried over sodium sulfate, filtered and the filtrate evaporated in vacuo, giving 14.9 g of a brown oil, identified as the desired product by NMR analysis. This oil is used without further treatment for the next step.

Step 3. 1-Dimethylamino-6-hydroxy indan.

A mixture of 1-dimethylamino-6-methoxy-indan (14.6 g) and 48% hydrobromic acid (140 ml) in glacial acetic (140 ml) is refluxed with stirring under N₂ for 3 hours. The cooled reaction mixture is poured into crushed ice and the pH adjusted to about 8–9 with 50% sodium hydroxide solution, resulting in the formation of an oil and a dark solid precipitate. The aqueous mixture is extracted with methylene chloride, the methylene chloride extract washed with H₂O and saturated sodium chloride solution, dried over sodium sulfate, filtered and the filtrate evaporated in vacuo, resulting in 9.6 g of a brown solid. The brown solid is dissolved in boiling toluene and the slightly cloudy supernatant decanted from a dark oily material. The toluene solution is cooled resulting in the formation of a precipitate which is filtered and allowed to air dry, resulting in 6.85 g of a beige crystalline solid, M.P. 141°–144° C. NMR indicates this to be the desired product, which is used without further treatment for the next reaction.

Step 4. 1-Dimethylamino-6-(3-N-phthalimidopropoxy)indan.

Potassium t-butoxide (4.3 g) is added to a stirred solution of the phenol obtained in the previous step (6.1 g) in dimethylformamide (60 ml). N-(3-bromopropyl)phthalimide (18.5 g) is added to the stirred solution, resulting in the formation of a brown suspension. The reaction mixture is stirred at RT for 48 hours. The reaction mixture is partitioned between ether and H₂O, the layers separated and the aqueous layer made more basic with 50% sodium hydroxide solution, and subsequently extracted with additional ether. The combined ether layers are washed with H₂O and stirred with 5% aqueous HCl. The ether layer is again washed with 5% aqueous HCl and the combined aqueous layers washed with methylene chloride. The acidic phase is made strongly alkaline with 50% sodium hydroxide solution and extracted with methylene chloride. The methylene chloride is washed with aqueous base and H₂O, dried over sodium sulfate, filtered and evaporated in vacuo, yielding 5.9 g of an amber oil, identified by NMR and IR analysis to be the desired phthalimido product.

Step 5. 6-(3-Aminopropoxy)-1-dimethylamino indan.

85% hydrazine hydrate solution (1.1 ml) is added to a suspension of 6-(3-N-phthalimidopropoxy)-1-dimethylamino indan (5.8 g) in absolute ethanol (55 ml). The reaction mixture is stirred at reflux for 3 hours, allowed to cool, and the mixture filtered. The filtered solid is washed with ethanol, the filtrate evaporated in vacuo and the residue triturated with 5% aqueous hydrochloric acid. The triturated solid is filtered and washed with 5% HCl. The filtrate is washed with ether and made strongly alkaline with 50% sodium hydroxide solution, resulting in the formation of an oily precipitate. The oil is extracted with diethyl ether and the ether washed with saturated sodium chloride solution. The combined aqueous layers are back-extracted with methylene chloride. The combined organic extracts are dried over sodium sulfate, filtered and the filtrate evaporated affording 3.2 g of an amber oil, identified by NMR to be the desired amine product.

Step 6. 3-Amino-4-[3-[6-(1-dimethylaminoindanyloxy)]-propylamino]-1,2,5-thiadiazole-1-oxide.

6-(3-Aminopropoxy)-1-dimethylamino indan (3.1 g) in methanol (60 ml) is added over a period of 90 minutes to a stirred solution of 3,4-dimethoxy-1,2,5-thiadiazole-1-oxide (2.15 g) in methanol (200 ml) under an atmosphere of $N_2$, while maintaining the reaction temperature at about 5° C. The reaction mixture is stirred for $2\frac{1}{2}$ hours, after which anhydrous ammonia (20 g) is bubbled into the reaction mixture over a period of 5 minutes. The reaction mixture is allowed to reach RT and stirred under $N_2$ overnight. The reaction mixture is evaporated in vacuo, affording 4.8 g of a foam which is dissolved in 5% methanol and methylene chloride and stirred at RT for 2 hours. The resulting cloudy solution is filtered and evaporated in vacuo. The residue is dissolved in 10% methanol in methylene chloride, placed on a silica gel column (150 g; 70–230 mesh) and eluted with successive concentrations of methanol in methylene chloride (10% to 40% methanol). The major fractions are pooled and evaporated in vacuo, resulting in 3.5 g of a foam, which is stirred in diethyl ether overnight. The resulting suspension is filtered and the solid washed with ether and dried at 60° C. at 5 mm Hg for 3 hours, resulting in 3.1 g of a white powder, M.P. 160°–162° C. (dec). NMR, IR and elemental analysis indicate that the white powder is the desired thiadiazole product.

Various tests in animals have been carried out to show the ability of the compounds of this invention to exhibit pharmacological responses that can be correlated with activity in humans. These tests involve such factors as the effect of the compounds of Formula I on gastric secretion and their $H_2$ antagonist and cytoprotective activity. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compounds or the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine anti-secretory properties.

The compounds of Formula I have been found to be histamine $H_2$-receptor antagonists by the results obtained in the following $H_2$-antagonist tests.

A. Isolated Guinea Pig Atria

The $H_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 111, *Molecular Pharmacology: The Mode of Action of Biologically Active Compound.* Vol. 1, Academic Press (1964).

1. Tissue Bath

A fifty ml jacketed tissue bath is maintained at 30° C. The bath consists of a Krebs-Henseleit buffer aerated with 95% $O_2$–5% $CO_2$, (pH 7.4). The buffer is prepared by mixing: 4 ml of an aqueous (distilled deionized) solution of $CaCl_2.2H_2O$ (0.37 g/ml); 4 ml of an aqueous (distilled deionized) solution of $MgSO_4.7H_2O$ (0.29 g/ml); 7.2 g of glucose; and, 2 liters of aqueous (distilled deionized) solution containing NaCl (28 g), $NaHCO_2$ (8.4 g), KCl (1.4 g) and $KH_2PO_4$ (0.6 g).

2. Preparation of Atria

Male albino guinea pigs (400–700 g, preferably 500–600 g) are killed by a blow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taper-point needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0 $\mu M$ histamine (0.1, 0.3, 1.0, 3.0, etc.) In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentration is 1.0 mM. If, however, no agonistic activity is observed when the concentrations has reached 100 $\mu M$ then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages (±SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH 10.0) is perfused and collected in 30 ml beakers. The beakers are changed every 10 or 15 minutes and the pH of these samples are recorded. Once the pH has stabilized around 6.5–7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225–231 (1979).

Male Sprague-Dawley rats 140–170 g are housed according to standard animal husbandry procedures. The rats are fasted twenty-four hours prior to testing. On the test day, rats are divided into groups of 5 or 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10X magnifying glass; the following scale is employed:

| Grade | Description |
| --- | --- |
| 0 | No lesions |
| 1 | 5 lesions, all < 2 mm |
| 2 | 5 lesions, at least 1 > 2 mm |
| 3 | 5–10 lesions, all < 2 mm |
| 4 | 5–10 lesions, at least 1 > 2 mm |
| 5 | 10 lesions, all < 2 mm |
| 6 | 10 lesions, at least 1 > 2 mm |
| 7 | Perforation |

The average ulcer severity (±S.E.) for each group of animals is calculated. The percent inhibition for each test compound is calculated as follows:

% inhibition =

$$\frac{\text{Mean value for control} - \text{Mean value for experimental}}{\text{Mean value for control}} \times 100$$

The compounds of Formula I have also been determined to exhibit cytoprotective activity.

The cytoprotective effectiveness of the compounds of Formula I is evaluated according to the following test procedure.

Male Sprague-Dawley rats 150–200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2N NaOH (1 ml) or 0.6N HCl (1ml), regardless of body weight. One hour after administration animals are sacrificed by cervical dislocation, their stomachs are removed, opened along the greater curvature, rinsed under running tap water and examined for lesions with a 2X–10X magnifying glass.

The reduction of lesion count, lesion severity score and ulcer index as compared to similar measurements made in the controls was expressed as a percentage. Measurement of statistical significance of the results was done by standard methods.

The average ulcer severity (±S.E.) for each group of animals is calculated. The percent inhibition for each test compound is calculated as follows:

% inhibition =

$$\frac{\text{Mean value for control} - \text{Mean value for experimental}}{\text{Mean value for control}} \times 100$$

The results of the anti-secretory, anti-ulcer and cytoprotective assays, detailed above, establish the anti-secretory activity, the $H_2$-receptor antagonist activity, the anti-ulcer activity, the cytoprotective activity, and the utility of the compounds of the present invention in the treatment of peptic ulcers in mammals, including humans. These compounds both aid in the healing of such ulcers and also prevent their formation.

A most preferred compound is 3-amino-5-[3-[5-[1-(N-piperidyl)-1,2,3,4-tetrahydronaphthyloxy]] propylamino]-1-methyl-1H-1,2,4-triazole.

In particular, the compounds according to Formulae I to VI are useful: in the treatment and prevention of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, H₁-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesiun stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day.

We claim:

1. A compound of the formula:

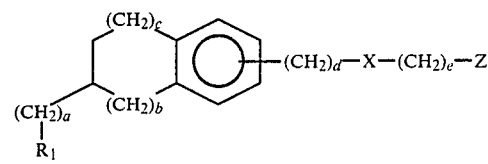

wherein:
a is 0, 1 or 2;
b is 0 or 1;
c is 1-b, 2-b or 3-b;
d is 0 or 1;
e is 2, 3 or 4;
X is oxygen, sulfur,

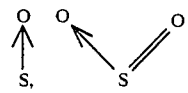

or $CH_2$;
Z is $-NHR_4$;
$R_1$ is $-NR_2R_3$;
$R_2$ and $R_3$ are each independently H or alkyl, or both together with the nitrogen to which they are attached form a 5, 6 or 7-membered ring which may include one to three additional hetero atoms of N, O or S;
$R_4$ is

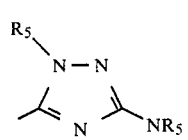

$R_5$ is H or lower alkyl;
or a pharmaceutically acceptable salt thereof.

2. A compound according to claim 1 wherein:
a is 0;
b is 0;
d is 0;
e is 3; and
X is oxygen.

3. A compound of the formula

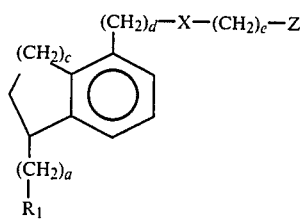

wherein:
a is 0, 1 or 2;
c is 1, 2 or 3;
d is 0 or 1;
e is 2, 3 or 4;
X is oxygen or sulfur;
Z is —NHR$_4$;
R$_1$ is —NR$_2$R$_3$;
R$_2$ and R$_3$ are each independently H or alkyl, or both together with the nitrogen to which they are attached form a 5, 6 or 7-membered ring which may include one to three additional hetero atoms of N, O or S;
R$_4$ is

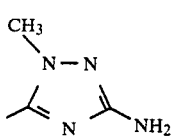

or a pharmaceutically acceptable salt thereof.

4. A compound of the formula

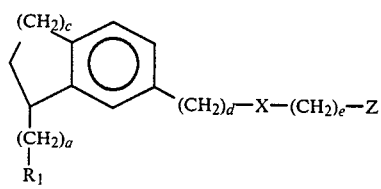

wherein:
a is 0, 1 or 2;
c is 1, 2 or 3;
d is 0 or 1;
e is 2, 3 or 4;
X is oxygen or sulfur;
Z is —NHR$_4$;
R$_1$ is —NR$_2$R$_3$;
R$_2$ and R$_3$ are each independently H or alkyl, or both together with the nitrogen to which they are attached form a 5, 6 or 7-membered ring which may include one to three additional hetero atoms of N, O or S;
R$_4$ is

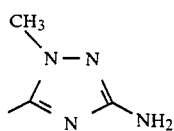

or a pharmaceutically acceptable salt thereof.

5. A compound of the formula

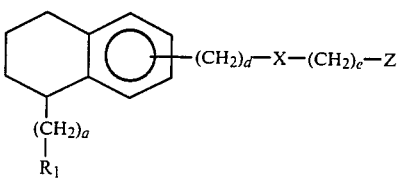

wherein:
a is 0, 1 or 2;
d is 0 or 1;
e is 2, 3 or 4;
X is oxygen or sulfur;
Z is —NHR$_4$;
R$_1$ is —NR$_2$R$_3$;
R$_2$ and R$_3$ are each independently H or alkyl, or both together with the nitrogen to which they are attached form a 5, 6 or 7-membered ring which may include one to three additional hetero atoms of N, O or
R$_4$ is

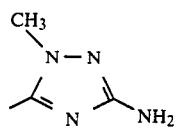

or a pharmaceutically acceptable salt thereof.

6. A compound of the formula

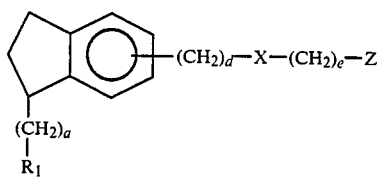

wherein:
a is 0, 1 or 2;
d is 0 or 1;
e is 2, 3 or 4;
X is oxygen or sulfur;
Z is —NHR$_4$;
R$_1$ is —NR$_2$R$_3$;
R$_2$ and R$_3$ are each independently H or alkyl, or both together with the nitrogen to which they are attached form a 5, 6 or 7-membered ring which may include one to three additional hetero atoms of N, O or S;
R$_4$ is

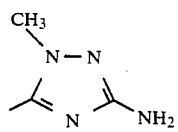

or a pharmaceutically acceptable salt thereof.

7. A compound according to claim 5 wherein:
a and d are 0;
e is 3; and
X is oxygen.

8. A compound according to claim 5 wherein:
a is 0;

d is 1;
e is 2; and
X is sulfur.

9. A compound of the formula

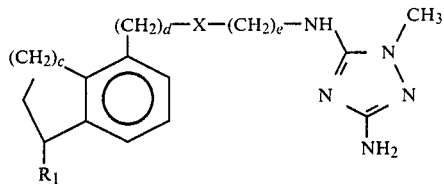

Formula VI wherein;
c is 1 or 2;
d is 0 or 1;
e is 2, 3 or 4;
X is oxygen or sulfur;
$R_1$ is $-NR_2R_3$;
$R_2$ and $R_3$ together with the nitrogen to which they are attached form a 5, 6 or 7 membered heterocyclic ring which may include on to three additional hetero atoms of N, O or S; or a pharmaceutically acceptable salt thereof.

10. A compound according to claim 9 wherein:
$R_1$ is N-piperidyl, N-pyrrolidinyl, N-morpholinyl or N-azepinyl.

11. A compound according to claim 9, which is 3-Amino-5-[3-[5-[1-(N-piperidyl)-1,2,3,4-tetrahydronaphthyloxy]]propylamino]-1-methyl-1H-1,2,4-triazole or a pharmaceutically acceptable salt thereof.

12. A compound according to claim 9, which is 3-Amino-5-[3-[5-[1-(N-morpholino)-1,2,3,4-tetrahydronaphthyloxy]]propylamino]-1-methyl-1H-1,2,4-triazole or a pharmaceutically acceptable salt thereof.

13. A compound according to claim 5, which is 3-Amino-5-[3-[5-(1-dimethylamino-1,2,3,4-tetrahydronaphthyloxy)]propylamino]-1-methyl-1H-1,2,4-triazole or a pharmaceutically acceptable salt thereof.

14. A compound according to claim 5, which is 3-Amino-5-[3-[7-(1-dimethylamino-1,2,3,4-tetrahydronaphthyloxy)]propylamino]-1-methyl-1H-1,2,4-triazole or a pharmaceutically acceptable salt thereof.

15. A compound according to claim 6, which is 3-Amino-5-[3-[4-[1-(N-piperidyl)indanyloxy]]-propylamino]-1-methyl-1H-1,2,4-triazole or a pharmaceutically acceptable salt thereof.

16. A compound according to claim 6, which is 3-Amino-5-[3-[4-(1-dimethylaminoindanyloxy)]-propylamino]-1-methyl-1H-1,2,4-triazole or a pharmaceutically acceptable salt thereof.

17. A compound according to claim 6, which is 3-Amino-5-[3-[6-[1-(N-piperidyl)indanyloxy]]-propylamino]-1-methyl-1H-1,2,4-triazole or a pharmaceutically acceptable salt thereof.

18. A method for decreasing acid secretion in the gastrointestinal tract of mammmals by administering thereto an anti-secretory effective amount of a compound according to claim 1.

19. A method for the treatment of gastrointestinal hyperacidity and ulceration in a mammal comprising administering thereto an effective amount of a compound according to claim 1.

20. A method for enhancing the gastrointestinal resistance to gastrointestinal irritants in humans and mammals comprising administering thereto an effective cytoprotective amount of a compound of the formula according to claim 1.

21. A pharmaceutical composition wherein the active ingredient is a compound according to claim 1 in admixture with a pharmaceutical carrier.

* * * * *

UNITED STATES PATENT AND TRADEMARK OFFICE
CERTIFICATE OF CORRECTION

PATENT NO. : 4,529,723
DATED : July 16, 1985
INVENTOR(S) : Donald E. Kuhla et al.

Page 1 of 2

It is certified that error appears in the above-identified patent and that said Letters Patent is hereby corrected as shown below:

Col. 2, line 35    In Formula I, "X" should read --Z--.

Col. 18    Scheme IV, the parts of which are separated by Schemes II and III, should appear as follows:

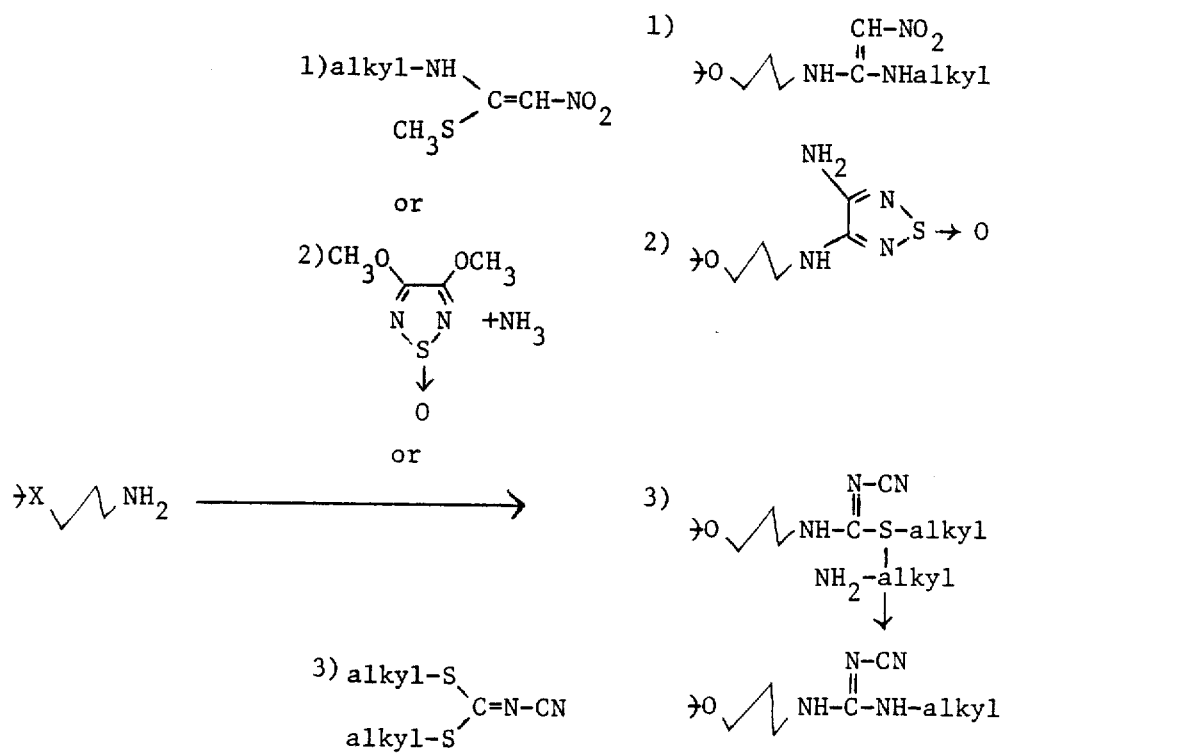

UNITED STATES PATENT AND TRADEMARK OFFICE
CERTIFICATE OF CORRECTION

PATENT NO.   : 4,529,723
DATED        : July 16, 1985
INVENTOR(S)  : Donald E. Kuhla et al.

It is certified that error appears in the above-identified patent and that said Letters Patent is hereby corrected as shown below:

Col. 19, line 66    "VI" should read --IV--.

Col. 21, line 3     "(19821)" should read --(1982)--.

Signed and Sealed this
Sixth Day of October, 1987

Attest:

DONALD J. QUIGG

Attesting Officer     Commissioner of Patents and Trademarks